US007291607B2

(12) United States Patent
Day et al.

(10) Patent No.: US 7,291,607 B2
(45) Date of Patent: Nov. 6, 2007

(54) **ISOMALTOOLIGOSACCHARIDES FROM *LEUCONOSTOC* AS NEUTRACEUTICALS**

(75) Inventors: Donal F. Day, Baton Rouge, LA (US); Chang-Ho Chung, Baton Rouge, LA (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 229 days.

(21) Appl. No.: 10/848,981

(22) Filed: May 19, 2004

(65) Prior Publication Data

US 2004/0235789 A1      Nov. 25, 2004

Related U.S. Application Data

(60) Provisional application No. 60/471,942, filed on May 20, 2003.

(51) Int. Cl.
*A61K 31/702* (2006.01)
*A61K 31/718* (2006.01)

(52) U.S. Cl. .......................... 514/61; 514/54; 514/60; 536/102

(58) Field of Classification Search .................. 514/54, 514/61
See application file for complete search history.

(56) References Cited

U.S. PATENT DOCUMENTS

| 4,013,510 A | 3/1977 | Frommer et al. ......... 195/31 R |
| 4,518,581 A * | 5/1985 | Miyake et al. ................ 424/48 |
| 5,141,858 A | 8/1992 | Paul et al. ..................... 435/97 |
| 5,840,705 A | 11/1998 | Tsukada et al. ............... 514/43 |
| 2004/0081711 A1 | 4/2004 | Rao et al. .................... 424/734 |

OTHER PUBLICATIONS

Jack et al., "The use of acarbose inhibition in the measurement of acid alpha-glucosidase activity in blood lymphocytes for the diagnosis of Pompe disease", (2006) Genetics in Medicine, vol. 8, No. 5, pp. 307-312.*
The Oxford Textbook of Oncology, 1995, published by Oxford University Press, pp. 447-453.*
Barrangou, R. et al,. "Functional and comparative genomic analyses of an operon involved in fructooligosaccharide utilization by *Lactobacillus acidophilus*," Proc. Natl. Acad. Sci. USA, vol. 100, pp. 8957-8962 (2003).
Chung, Chang-Ho, "A potential nutraceutical from *Leuconostoc mesenteroides* B-742 (ATCC 13146); Production and Properties," A dissertation submitted to the Department of Food Science, Louisiana State University, May 2002.
Day, D.F. et al., "Probiotics from Sucrose," a slide presentation at the May 22, 2002 meeting of the American Society of Microbiologists.

Juven, B.J. et al., "Antagonistic effects of *lactobacilli* and *pediococci* to control intestinal colonization by human enteropathogens in live poultry," J. Appl. Bacteriol., vol. 70, pp. 95-103 (1991).
Kim, C.Y. et al., "Production of mannitol using *Leuconostoc mesenteroides* NRRL B-1149," Biotechnol. Bioprocess Eng., vol. 7, pp. 234-236 (2002).
Naughton, P.J. et al., "Effects of nondigestible oligosaccharides on *Salmonella enterica* Serovar Typhimurium and nonpathogenic *Escherichia coli* in the pig small intestine in vitro," Appl. Environ. Microbiol., vol. 67, pp. 3391-3395 (2001).
Paul, F., "Acceptor reaction of a highly purified dextransucrase with maltose and oligosaccharides. application to the synthesis of controlled-molecular-weight dextrans," Carbohydr. Res., vol. 149, pp. 433-441 (1986).
Robyt, J.F., "Dextran," In: Encyclopedia of Polymer Science and Engineering, (H.F. Mark et al., eds.), vol. 4, pp. 752-767, John Wiley & Sons, New York (1986).
Yoo, S.K., The production of glucooligosaccharides by *Leuconostoc mesenteroides* ATCC 13146 and *Lipomyces starkeyi* ATCC 74054, Ph.D. Dissertation, Louisiana State University (1997).
Yoo, S.K. et al., Co-production of dextran and mannitol by *Leuconostoc mesenteroides*, J. Microbiol. Biotechnol., vol. 11, pp. 880-883 (2001).
Yoo, S.K. et al., Highly branched glucooligosaccharide and mannitol production by mixed culture fermentation of *Leuconostoc mesenteroides* and *Lipomyces starkeyi*, J. Microbiol. Biotechnol., vol. 11, pp. 700-703 (2001).
Bailey, J.S. et al., "Effect of fructooligosaccharide on *Salmonella* colonization of the chicken intestine," Poultry Sci., vol. 70, pp. 2433-2438 (1991).
Chou, C-C. et al., "Growth of bifidobacteria in soymilk and their survival in the fermented soymilk drink during storage," Int. J. Food Microbiol., vol. 56, pp. 113-121 (2000).

(Continued)

*Primary Examiner*—Shaojia Anna Jiang
*Assistant Examiner*—Eric S Olson
(74) *Attorney, Agent, or Firm*—Bonnie J. Davis; John H. Runnels

(57) ABSTRACT

Isomaltooligosaccharides (IMOs) produced by *Leuconostoc mesenteroides* ATCC 13146 fermentation with a sucrose:maltose ratio of 2:1 have been discovered to be effective prebiotics in mixed cultures of microbial populations, including cultures from chicken ceca. Surprisingly in mixed microbial cultures this IMO composition proved as effective as FOS. Thus, these IMOs can be used as effective prebiotics for both birds and mammals. Moreover, the IMOs were discovered to be effective non-competitive inhibitors of α-glucosidase. These IMOs also will be useful, as an α-glucosidase inhibitor, in a therapeutic application for several diseases, including obesity, diabetes mellitus, pre-diabetes, gastritis, gastric ulcer, duodenal ulcer, caries, cancer, viral disease such as hepatitis B and C, HIV, and AIDS. A diet with 5-20% IMOs was also shown to reduce the abdominal fat tissue in mammals.

2 Claims, 12 Drawing Sheets

OTHER PUBLICATIONS

Cote, G.L. et al., "The formation of a-D-(1,3) branch linkages by an exocellular glucansucrase from *L. mesenteriodes* NRRL B-742," Carbohyd. Res., vol. 119, pp. 141-156 (1983).

Djouzi, Z. et al., "Degradation and fermentation of α-gluco-oligosaccharides by bacterial strains from human colon: in vitro and in vivo studies in gnotobiotic rats," J. Appl. Bact., vol. 79, pp. 117-127 (1995).

Djouzi, Z.et al., "Compared effects of three oligosaccharides on metabolism of intestinal microflora in rats inoculated with a human faecal flora," Br. J. Nutr., vol. 78, pp. 313-324 (1997).

Flickinger, E.A. et al., "Glucose-based oligosaccharides exhibit different in vitro fermentation patterns and affect in vivo apparent nutrient digestibility and microbial populations in dogs," J. Nutr., vol. 130, pp. 1267-1273 (2000).

Fukata, T. et al., "Inhibitory effects of competitive exclusion and fructooligosaccharide, singly and in combination, on *Salmonella* colonization of chicks," J. Food. Prot., vol. 62, pp. 229-233 (1999).

Gibson, G.R. et al., "Bifidogenic properties of different types of fructo-oligosaccharides," Food Microbiol., vol. 11, pp. 491-498 (1994).

Gmeiner, M. et al., "Influence of a symbiotic mixture consisting of *Lactobacillus acidophilus* 72-4 and a fructooligosaccharide preparation on the microbial ecology sustained in a simulation of the human intestinal microbial ecosystem (SHIME reactor)," Appl. Microbiol. Biot., vol. 53, pp. 219-223 (2000).

Kaplan, H. et al., "Fermentation of fructooligosaccharides by lactic acid bacteria and bifidobacteria," Appl. Environ. Microbiol., vol. 66, pp. 2682-2684 (2000).

Koepsell, H.J. et al., "Enzymatic synthesis of dextran. acceptor specificity and chain initiation," J. Biol. Chem., vol. 200, pp. 793-801 (1952).

Kohmoto, T. et al., "Effect of isomalto-oligosaccharides on human fecal flora Bifidobacteria," Microflora, vol. 7, pp. 61 69 (1988).

Loo, J.V. et al., "Functional food properties of non-digestible oligosaccharides: a consensus report from the ENDO project (DGXII AIRII-CT94-1095)," Brit. J. Nutr., vol. 81, pp. 121-132 (1999).

Monsan, P. et al., "Oligosaccharide feed additives," In: R.J. Wallace and A. Chesson (eds) *Biotechnology in animal feeds and animal feeding*, pp. 233-245, VCH Velagsgesellschaft mbH, Weinheim, Germany (1995).

Oyofo, B. et al., "Effect of carbohydrates on *Salmonella typhimurium* colonization in broiler chickens," Avian Dis., vol. 33, pp. 531-534 (1989).

Remaud, M. et al., "Characterization of α-1,3 branched oligosaccharides synthesized by acceptor reaction with the extracellular glucosyltransferases from *L. mesenteriodes* NRRL B-742," J. Carbohyd. Chem., vol. 11, pp. 359-378 (1992).

Robyt, J. et al., "Relative, quantitative effects of acceptors in the reaction of *Leuconostoc mesenteroides* B-512F dextransucrase," Carbohydr. Res., vol. 121, pp. 279-286 (1983).

Tomomatsu, H., "Health effects of oligosaccharides," Food Technol., vol. 48, pp. 61-65 (1994).

Valette, P. et al., "Bioavailability of new synthesized glucooligosaccharides in the intestinal tract of gnotobiotic rats," J. Sci. Food Agric., vol. 62, pp. 121-127 (1993).

\* cited by examiner galactooligosacchrides disaccharide

US 7,291,607 B2

ISOMALTOOLIGOSACCHARIDES FROM *LEUCONOSTOC* AS NEUTRACEUTICALS

The benefit of the May 20, 2003 filing date of provisional application Ser. No. 60/471,942 is claimed under 35 U.S.C. §119(e).

This invention pertains to the use of maltosyl-isomaltooligosaccharides as a dietary supplement for birds and mammals, specifically, to promote the growth of beneficial intestinal microbes, inhibit the growth of pathogenic intestinal microbes, and for therapeutic intervention in diseases such as diabetes by inhibiting the activity of α-glucosidase to slow the rate of glucose release from carbohydrates and thereby reduce the uptake of glucose.

Prebiotics are nondigestible food ingredients that selectively stimulate the growth and/or activity of beneficial microbial strains (probiotics) residing in the host intestine. See R. Barrangou et al, "Functional and comparative genomic analyses of an operon involved in fructooligosaccharide utilization by *Lactobacillus acidophilus*," Proc. Natl. Acad. Sci. USA, vol. 100, pp. 8957-8962 (2003). It is believed the ability of these probiotics to catabolize oligosaccharides (two to ten monosaccharide units linked with glycosidic bonds) is a key factor in bestowing beneficial health effects. Certain oligosaccharides are used as prebiotics. They are resistant to metabolism and adsorption in the small intestine and ultimately positively influence the composition of microflora in the large intestine. Oligosaccharides are also widely used in foods such as soft drinks, cookies, cereals, candies, and dairy products. Other applications for oligosaccharides such as an anti-cariogenic agent or a low sweetness humectant have been explored. See S. K. Yoo, "The production of glucooligosaccharides by *Leuconostoc mesenteroides* ATCC 13146 and *Lipomyces starkeyi* ATCC 74054, Ph.D. Dissertation, Louisiana State University (1997).

Oligosaccharides used as prebiotics are currently produced either by extraction from plant sources, acid or enzymatic hydrolysis of polysaccharides or enzymatic synthesis by transglycosylation reactions. See P. Monsan et al., "Oligosaccharide feed additives," In: R. J. Wallace and A. Chesson (eds) Biotechnology in animal feeds and animal feeding, pp.233-245, VCH Velagsgesellshaft mbH, Weinheim, Germany (1995).

Types of Oligosaccharides

Types of oligosaccharides include fructooligosaccharides (FOS), glucooligosaccharides (GOS), and α-galactooligosaccharides. The differences in structures are illustrated in FIG. 1. Fructooligosaccharides (FOS) have attracted serious commercial interest as prebiotics. They are composed of a D-glucopyranose unit at the non-reducing end (G) linked via an α-1,2 linkage to two or more β-2,1-linked fructosyl units (F). This group includes 1-kestose (GF2), nystose (GF3), and IF-fructofuranosyl nystose (GF4). Many of the oligosaccharides marketed commercially are FOS, e.g., Raftilose and Nutraflora in the United States.

α-Galactooligosaccharides, which are α-galactosyl derivatives of sucrose, are present in many legume seeds. Mono-, di-, and tri-α-galactosylsucrose, known respectively as raffinose, stachyose, and verbascose, are produced by extraction from plants, particularly soybeans. These oligosaccharides are known to be, in part, responsible for the flatulence and diarrhea that follows consumption of beans, because of the absence of an α-galactosidase in the gastrointestinal tracts of humans and animals.

Glucooligosaccharides (GOS) is a generic term for polyglucose oligomers. GOS may contain a number of different linkages and are generally obtained from starch hydrolysates (maltose and maltodextrins) through the action of the α-transglucosidase (EC 2.4.1.24) from *Aspergillus* sp. Glucooligosaccharides can also be produced by restricting polymer size during the fermentation process. A subcategory of GOS is the α-isomaltooligosaccharides (IMO) which contain α-1,6 bonds in their main chain. See H. J. Koepsell et al., "Enzymatic synthesis of dextran acceptor specificity and chain initiation," J. Biol. Chem., vol. 200, pp. 793-801 (1952). Dextransucrase (EC 2.4.1.5), an enzyme produced mainly by species of *Leuconostoc* and *Streptococcus*, catalyzes the synthesis of high molecular weight glucans (dextrans).

Oligosaccharides as Prebiotics

Ingested oligosaccharides (prebiotics) are capable of reaching the colon without being digested. It has been proposed that fructooligosaccharides are preferentially utilized by *Lactobacilli* and *Bifidobacterial* species which are considered beneficial species of the human intestinal tract. See H. Kaplan et al., "Fermentation of fructooligosaccharides by lactic acid bacteria and *Bifidobacteria*," Appl. Environ. Microbiol., vol. 66, pp. 2682-84 (2000). Substituting fructooligosaccharides as a carbon source would preferentially increase the concentration of *Lactobacillus* and *Bifidobacteria* species with a concomitant rise in the intestinal production of lactic acid and short-chain fatty acids (SCFA). Both these products would have the net effect of lowering the pH in the large intestine. This appears to be one mode by which beneficial species can out-complete and indeed help prevent the establishment of undesirable pathogenic organisms such as *Salmonella*. See B. J. Juven et al., "Antagonistic effects of *Lactobacilli* and *Pediococci* to control intestinal colonization by human enteropathogens in live poultry," J. Appl. Bacteriol., vol. 70, pp. 95-103 (1991). The fructooligosaccharides may also interact with carbohydrate receptors present on the surface of either microbial or epithelial cells, affecting cell adhesion and immunomodulation. See P. J. Naughton et al., "Effects of nondigestible oligosaccharides on *Salmonella enterica* Serovar *Typhimurium* and nonpathogenic *Escherichia coli* in the pig small intestine in vitro," Appl. Environ. Microbiol., vol. 67, pp. 3391-95 (2001).

Fructooligosaccharides, galactooligosaccharides, and soybean oligosaccharides were found not to be digested by enzymes secreted by small intestine, but to be fermented by certain microorganisms found in human and livestock intestines, especially by the *Bifidobacterium* sp. See. H. Tomomatsu, "Health effects of oligosaccharides," Food Technol., vol. 48, pp. 61-65 (1994). There are numerous reports regarding the stimulating effects of fructooligosaccharides on the growth of probiotic strains. See P. Monsan et al., 1995; and M. Gmeiner et al., "Influence of a symbiotic mixture consisting of *Lactobacillus acidophilus* 72-4 and a fructooligosaccharide preparation on the microbial ecology sustained in a simulation of the human intestinal microbial ecosystem (SHIME reactor)," Appl. Microbiol. Biot., vol. 53, pp. 219-223 (2000). Dietary FOS have been reported to be effective in reducing the numbers of the harmful bacteria, *E. coli*, in the intestine of piglets, but did not reduce numbers of *Salmonella*. See P. J. Naughton et al., "Effects of nondigestible oligosaccharides on *Salmonella enterica* Serovar *Typhimurium* and nonpathogenic *Escherichia coli* in the pig small intestine in vitro," Appl. Environ. Microbiol., vol. 67, pp. 3391-95 (2001). However, in the same study, commercially available glucooligosaccharides (GOS), another oligosaccharide, showed no effect on either genus of bacteria.

In studies of in vitro fermentation characteristics using human fecal material, small intestinal digestibility, and effects on fecal microbial populations in dogs, GOS (containing α-1,2, α-1,4 and α-1,6 linkages) and FOS produced short chain fatty acids in human fecal material more rapidly than other substrates, such as gum arabic, guar gum and guar hydrolysate. GOS also appeared to be indigestible in the small intestine, while supplying a carbon source for bacterial fermentations in the large intestine of cannulated dogs. See E. A. Flickinger et al., "Glucose-based oligosaccharides exhibit different in vitro fermentation patterns and affect in vivo apparent nutrient digestibility and microbial populations in dogs," J. Nutr., vol. 130, pp. 1267-1273 (2000). When the viable count of *Bifidobacterium infantis* and *B. longum*, and changes in pH due to various carbohydrate-supplemented soymilks were monitored, *B. longum* showed a significantly (P<0.05) higher count on a crude isomaltooligosaccharide (75%) supplemented soymilk than in the control (soymilk without the added supplement) at the end of fermentation. See C-C. Chou et al., "Growth of *Bifidobacteria* in soymilk and their survival in the fermented soymilk drink during storage," Int. J. Food Microbiol., vol. 56, pp. 113-121 (2000). Another study showed that GOS was only 20% digested by germfree rats. See P. Valette et al., "Bioavailability of new synthesized glucooligosaccharides in the intestinal tract of gnotobiotic rats," J. Sci. Food Agric., vol. 62, pp. 121-127 (1993). Dietary isomaltooligosaccharides (13.5 g/day for 14 days) were reported to increase fecal *Bifidobacteria* levels (P<0.05) in healthy adult males. See T. Kohmoto et al., "Effect of isomalto-oligosaccharides on human fecal flora *Bifidobacteria*," Microflora, vol. 7, pp. 61 69 (1988). Another study investigated the ability of several human gut bacteria to break the α-1,2 and α-1,6 glycosidic linkages in α-glucooligosaccharides, in vitro, in substrate utilization tests. See Z. Djouzi et al., "Degradation and fermentation of α-gluco-oligosaccharides by bacterial strains from human colon: in vitro and in vivo studies in gnotobiotic rats," J. Appl. Bact., vol. 79, pp. 117-127 (1995). Branched oligomers were resistant to both gastrointestinal enzymes and utilization by pathogenic microorganisms. They also reported that α-1,2 glucosidic bonds were more resistant than α-1,6 linkages in kinetic studies of glucooligosaccharide hydrolysis in pH-regulated fermentations. This study indicated the differences in utilization, and thus effectiveness, of GOS based on types and degree of branching.

Production of Glucooligosaccharides

Glucansucrases have been extensively studied because of their role in the production of dextran and its role in the cariogenic process. Glucansucrases (EC 2.4.5.1), usually extracellular but in some cases cell-associated, are primarily produced by various species of soil bacteria. Those produced by *Leuconostoc* sp. are called dextransucrase. Those produced by *Streptococcus* sp. and other lactic bacteria, *Lactococci*, are called glucosyltransferases. Streptococcal glucansucrases synthesize primarily α-1,3 rich polysaccharides. *Leuconostoc* glucansucrases produce α-1,6 rich polysaccharides.

Glucansucrases catalyze the synthesis of high molecular weight D-glucose polymers from sucrose. In the presence of efficient acceptors, e.g., maltose, they may catalyze the synthesis of low molecular weight oligosaccharides. See F. Paul, "Acceptor reaction of a highly purified dextransucrase with maltose and oligosaccharides: Application to the synthesis of controlled-molecular-weight dextrans," Carbohydr. Res., vol. 149, pp. 433-441 (1986).

Dextransucrases catalyze the synthesis of high molecular weight glucans (dextrans) according to the reaction:

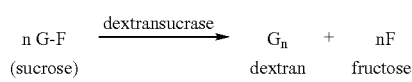

Dextran is a D-glucose polymer composed mainly of α-1,6 linked backbones in a linear chain and α-1,2, α-1,3, and/or α-1,4 branch linkages. See U.S. Pat. No. 5,229,277. The chemical structure of the dextran is specific to the glucansucrase of the producing strain of microbes (Table 1). See J. F. Robyt, "Dextran," In: Encyclopedia of Polymer Science and Engineering," (H. F. Mark et al., eds.), Vol. 4, pp. 752-767, John Wiley & Sons, New York (1986). The dextransucrase from *L. mesenteroides* NRRL B-1299 can produce α-glucooligosaccharides (GOS) containing one or more D-glucopyranosyl branch units linked via α-1,2 glycosidic bonds if maltose supplied as an acceptor. See F. Paul et al., "Method for the production of α-1,2 oligodextrans using *Leuconostoc mesenteroides* B-1299," U.S. Pat. No. 5,141,858. However, dextransucrase from *L. mesenteroides* B-742 (ATCC 13146) produces two dextrans; one with α-1,6 and α-1,3 linkages, and another with α-1,6 and α-1,4 linkages. (Table 1) Usually a high molecular weight dextran ($10^6$-$10^7$ Da) is produced. This is the case, for example, of the enzyme from *L. mesenteroides* NRRL-512F, which is used to produce dextran polymers of industrial interest including chromatography supports, photographic emulsions, iron carriers, and blood plasma substitutes (Robyt, 1986).

TABLE 1

Linkages in different dextrans as obtained by methylation analysis

| | | Linkages % | | | | |
|---|---|---|---|---|---|---|
| Dextran[a] | Solubility | α-1→6 | α-1→3 | α-1→3 Br[b] | α-1→2 Br[b] | α-1→4 Br[b] |
| L. m. B-512F | Soluble | 95 | 5 | | | |
| L. m. B-742 | Soluble | 50 | | 50 | | |
| L. m. B-742 | Less soluble | 87 | | | | 13 |
| L. m. B-1299 | Soluble | 65 | | | 35 | |
| L. m. B-1299 | Less soluble | 66 | | 1 | 27 | |
| L. m. B-1355 | Soluble | 54 | 35 | 11 | | |
| L. m. B-1355 | Less soluble | 95 | | 5 | | |
| S. m. 6715 | Soluble | 64 | | 36 | | |
| S. m. 6715 | Insoluble | 4 | 94 | 2 | | |

[a]L. m., *Leuconostoc mesenteroides*; S. m., *Streptococcus mutans*.
[b]Br, Branch linkage. Adapted from Robyt, 1986.

The synthesis of oligosaccharides using dextransucrase can be induced at the expense of dextran synthesis. In the presence of sucrose, the introduction into the reaction medium of molecules, like maltose, isomaltose, and O-α-methylglucoside, shifts the pathway of glucan synthesis towards the production of oligosaccharides. See Paul, 1986; and M. Remaud et al., "Characterization of α-1,3 branched oligosaccharides synthesized by acceptor reaction with the extracellular glucosyltransferases from *L. mesenteriodes* NRRL B-742," J. Carbohyd. Chem., vol. 11, pp. 359-378 (1992); Koepsell et al., 1952; and J. Robyt et al., "Relative, quantitative effects of acceptors in the reaction of *Leuconostoc mesenteroides* B-512F dextransucrase," Carbohydr. Res., vol. 121, pp. 279-286 (1983). The molecular weight and polydiversity of this oligosaccharide product are dependent upon the sucrose to acceptor ratio, the strain of bacteria, and on the characteristics of the intermediate oligosaccharides in the reaction. The ratio of sucrose to maltose affects the composition and yield of the oligosaccharides produced by the acceptor reaction. When the maltose to sucrose ratio was 2, a partially purified dextransucrase from *L. mesenteroides* NRRL B-512F produced 85% of the theoretical yield of polysaccharide as oligosaccharides, with an average degree of polymerization (DP) of 4. See U.S. Pat. No. 5,141,858; and Paul, 1986.

*Leuconostoc mesteroides* B-742 ATCC 13146

*Leuconostoc mesenteroides* ATCC 13146 was isolated from spoiled canned-tomatoes. (Robyt, 1986) The dextran produced by this (B-742) *Leuconostoc* strain is highly branched, containing as much as 50% α-1,3 linkages. *Leuconostoc mesenteroides* ATCC 13146 actually produces two exocellular α-D-glucans, a fraction L, which is precipitated at an ethanol concentration of 39%, and a fraction S, which is precipitated at a concentration of 45% ethanol (Robyt, 1986). Fraction L consists of an α-1,6 backbone with α-1,4 branch-points, and fraction S consists of an α-1,6 backbone with α-1,3 branch-points. The L fraction from *Leuconostoc mesenteroides* ATCC 13146 contains 87% α-1,6 linkages and 13% α-1,4 linkages. The percentage of α-1,3 branch-points in the fraction S glucan is variable, dependant on the conditions under which it is synthesized from sucrose. The α-1,3 linkages of the S fraction of *L. mesenteroides* ATCC 13146 are all branched linkages. This dextran demonstrates extreme resistance to endodextranase. This property seems related to its structure that has the highest possible degree of branching and exhibits a comb-like structure with main chains of consecutive α-1,6 linked glucose residues to which single α-1,3 linked glucosyl residues are attached. Any change in reaction conditions that affects the rate of acceptor reaction relative to chain elongation also affects the degree of branching in ATCC 13146 fraction S dextran.

The acceptor reaction of *L. mesenteroides* ATCC 13146 was investigated and found that branch formation in this strain, when maltose was the acceptor, was dependant upon reaction conditions. *L. mesenteroides* ATCC 13146 in the presence of maltose produced 90% of the theoretical yield of polymer as isomaltooligosaccharides, under optimum conditions for sucrose fermentation. See Yoo, 1997; S. K. Yoo et al., "Co-production of dextran and mannitol by *Leuconostoc mesenteroides*, J. Microbiol. Biotechnol., vol. 11, pp. 880-883 (2001); and S. K. Yoo et al., "Highly branched glucooligosaccharide and mannitol production by mixed culture fermentation of *Leuconostoc mesenteroides* and *Lipomyces starkeyi*, J. Microbiol. Biotechnol., vol. 11, pp. 700-703 (2001). The fermentation was essentially complete in 24 hours, with oligosaccharide production being linked to growth. The production rate was about 0.9 g/L hr. The maltose to sucrose ratio was able not only to alter the yield of oligosaccharide but also to change the relative proportion of different size oligosaccharides produced by the fermentation. The highest yields of isomaltooligosaccharides were obtained when the ratio of sucrose to maltose in the fermentation was two. This is the same ratio reported for optimum oligosaccharide production in vitro by the dextransucrase of *L. mesenteroides* B-512F (See Paul et al., 1986). Several *Leuconostoc* strains were tested to check for oligosaccharide size profiles produced in response to maltose, because individual *Leuconostoc* species synthesize different dextransucrases in response to various acceptors. The isomaltooligosaccharides produced by *L. mesenteroides* ATCC 13146 were mostly DP (degree of polymerization) 3-5 by chemical analysis. Isomaltooligosaccharides prepared by alcohol-precipitated, cell-free culture broths had greater amounts of higher branched isomaltooligosaccharides up to DP 7, than commercial preparations and had no glucose and less maltose (Yoo, 1997). These isomaltooligosaccharides were found to affect isolated, single microbial cultures by suppressing growth of *Salmonella enteritidis, Salmonella typhimurium, Staphylococcus aureus, Staphylococcus epidermidis*, and *Clostridium perfringenes*, and supporting growth of two *Bifidobacterium* species. (Yoo, 1997).

D-mannitol is a sugar-alcohol derived from mannose or fructose by dehydrogenation. In sucrose fermentations, mannitol is produced as an end product, as fructose can be used as an electron acceptor, but the levels of mannitol produced vary with the strain. See Yoo, 1997; and C. Y. Kim et al., "Production of mannitol using *Leuconostoc mesenteroides* NRRL B-1149," Biotechnol. Bioprocess Eng., vol. 7, pp. 234-236 (2002). Mannitol was found as one of the major end products in this *Leuconostoc* fermentation. It is necessary to separate the mannitol from the oligosaccharides if they are to be used as prebiotics, because mannitol can act as an additional carbon source. Its presence would hinder the ability to ascribe the essential and unique role of oligosaccharides on intestinal microflora. (Yoo, 1997)

Oligosaccharides as Antibiotic Alternatives in Animals

Antibiotic resistance among known pathogens such as *Salmonella* and *Escherichia coli* is expanding due to the wide use of antibiotics in areas ranging from medicine to animal feed. Although only specific antibiotics are used in feed preparations and are exclusive to non-human use, their chemical similarity to antibiotics prescribed for humans has raised concern that resistance will spread more rapidly, since resistant mechanisms generally affect an entire class of antibiotics (ex: penicillinases to inhibit the Penicillins). This, coupled with public pressure to remove antibiotics from animal feeds, has created a need for safe alternatives that can effectively control the growth of bacterial pathogens in the human food supply. Selected fructooligosaccharides and glucooligosaccharides have shown potential as alternatives to antibiotics. See P. Monsan et al., (1995); J. V. Loo et al., "Functional food properties of non-digestible oligosaccharides: a consensus report from the ENDO project (DGXII AIIUI-CT94-1095)," Brit. J. Nutr., vol. 81, pp: 121-132 (1999); and P. Valette et al., "Bioavailability of new synthesized glucooligosaccharides in the intestinal tract of gnotobiotic rats," J. Sci. Food Agric., vol. 62, pp. 121-127 (1993). However, not all oligosaccharides have been found effective. Although FOS is generally considered to be effective in regulating and reducing pathogenic microbial populations, conflicting reports exist about the effectiveness of GOS. See Naughton et al., 2001; and Yoo, 1997. These conflicting reports may be due to variability in the composition of the GOS (the degree of branching, the size, the amount of mannitol, or the acceptor used in fermentation production), or whether the GOS was tested on single microbial cultures, mixed microbial cultures, or in vivo. There may also be differences depending on the animal tested.

During recent years, poultry production and consumption have continually increased. Since 1992, the production of broilers grew from 9,482,000 to 14,017,000 tons in 1996 in the United States. Poultry is a carrier of numerous bacteria, including *Salmonella* and *Campylobacter*. Practical experience has demonstrated the difficulty in reducing the incidence of *Salmonella* on chickens once they arrive at the processing plant. Significant reduction in *Salmonella* on processed carcasses requires the delivery of chickens with reduced *Salmonella* to the processing plant. One of the possible ways to control *Salmonella* outbreaks may be through the judicious addition of selected carbohydrates to the diet of chickens. Mannose and lactose in the diet of chickens have been reported to reduce *Salmonella* colonization. See B. Oyofo et al., "Effect of carbohydrates on *Salmonella typhimurium* colonization in broiler chickens," Avian Dis., vol. 33, pp. 531-534 (1989). Fructooligosaccharides (FOS) have been shown to influence intestinal bacterial populations by enhancing the growth of lactic acid bacteria such as *Lactobacillus* species and *Bifidobacteria*, and to inhibit *Salmonella* colonization of chicks. See J. S. Bailey et al., "Effect of fructooligosaccharide on *Salmonella* colonization of the chicken intestine," Poultry Sci., vol. 70, pp. 2433-2438 (1991); and T. Fukata et al., "Inhibitory effects of competitive exclusion and fructooligosaccharide, singly and in combination, on *Salmonella* colonization of chicks," J. Food. Prot., vol. 62, pp. 229-233 (1999). The mean number of *Salmonella enteritidis* in the chicks of the fructooligosaccharide group was significantly (P<0.05) decreased compared with the control group. There are no reports that a glucooligosaccharide is effective in modifying the gut microflora in poultry.

Importance of α-Glucosidase Inhibition

Starch is one of the most readily available fermentable sources of energy for organisms and makes up 60-70% of the dietary carbohydrate consumption in humans. Humans secrete a pancreatic α-amylase that cleaves starch to a di-(maltose), tri-(maltotriose), and branched α-dextrins in the duodenal cavity. Because there is no integral transport process in the intestinal enterocyte that can accommodate anything larger than free glucose, these oligosaccharides are further processed to glucose in the intestinal surface membrane by α-glucosyl saccharidases, including α-glucosidase. These enzymes form part of a large glycoprotein component of the intestinal surface brush border membrane. Once formed, glucose then may be cotransported into the enterocyte, along with $Na^+$, either by a 75 kDa specific integral brush border glucose carrier or by a transporter expressed in the small intestine. Inhibitors of α-glucosidase are know to delay the digestion of starch, of starch-derived oligosaccharides, and sucrose such that the rise in blood sugar levels is slowed and insulin secretion is decreased after a meal. These inhibitors have been proposed to be used therapeutically for obesity, gastritis, gastric ulcer, duodenal ulcer, caries, hyperglycemia, hyperinsulinemia, diabetes mellitis, cancer, viral infection, hepatitis B and C, HIV and AIDS. See U.S. Pat. Nos. 5,840,705; and 4,013,510; and U.S. Patent Application No. 2004/0081711. At least two commercial oral α-glucosidase inhibitors, Miglitol and acarbose, are currently prescribed for use in managing non-insulin-dependent diabetes mellitus by slowing the appearance of glucose in the blood after eating.

We have discovered that the isomaltooligosaccharides (IMOs) produced by *Leuconostoc mesenteroides* ATCC 13146 fermentation with a sucrose to maltose ratio of 2:1 are effective prebiotics in mixed cultures of microbial populations, including cultures from chicken ceca. Surprisingly in mixed microbial cultures, this IMO composition proved as effective as FOS as a potential prebiotic. This IMO composition could be an effective alternative to antibiotics for chickens and other poultry. Thus, these IMOs can be used as effective prebiotics for both birds and mammals. Moreover, the IMOs were discovered to be effective non-competitive inhibitors of α-glucosidase. These IMOs also will be useful, as an α-glucosidase inhibitor, in a therapeutic application for several diseases, including obesity, diabetes mellitus, prediabetes, gastritis, gastric ulcer, duodenal ulcer, caries, cancer, viral disease such as hepatitis B and C, HIV, and AIDS. A diet with 5-20% IMOs was also shown to reduce the abdominal fat tissue in mannals.

Figure 1:
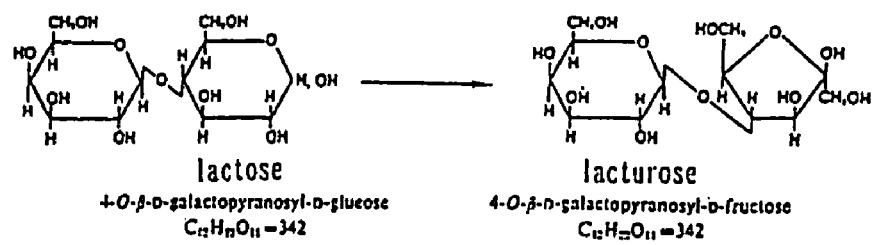
FIG. 1 illustrates the structures of various oligosaccharides.
Figure 1:
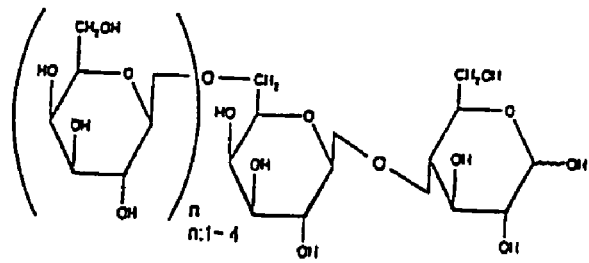
Figure 1:
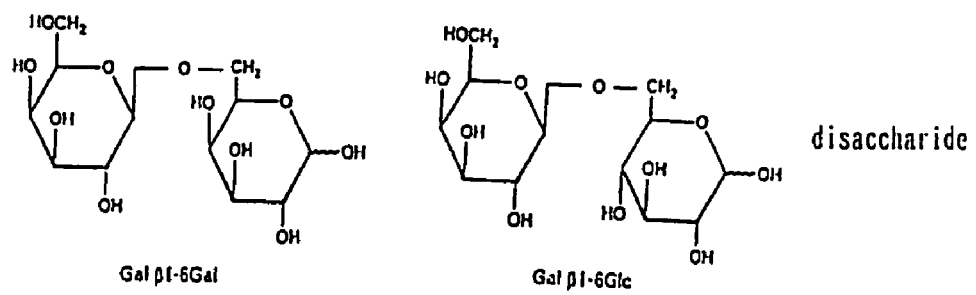
Figure 1:
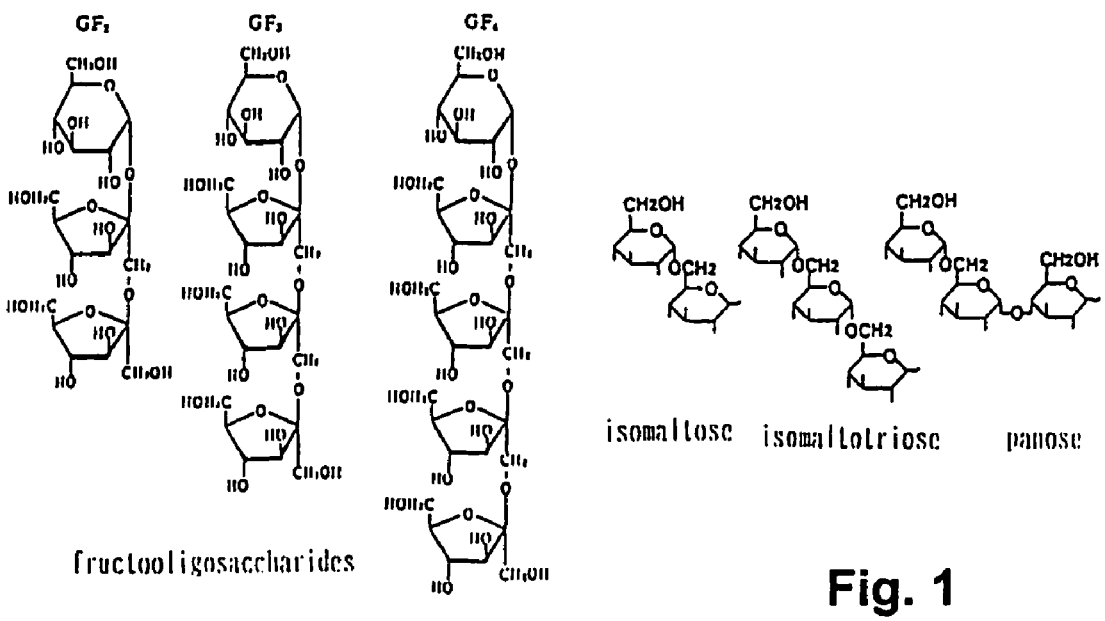

*rium longum* at different concentrations of panose (branched; α-1,4 and α-1,6) and maltooligosaccharides (M.O.; d.p. 4-10).

The present invention describes the production and application of mixtures of isomaltooligosaccharides (IMOs) ranging in size from DP (degree of polymerization) 3 to 7 units and incorporating a maltosyl group at the reducing end of each oligomer. The said mixtures were produced by fermentation with *Leuconostoc mesenteroides* ATCC 13146 by restricting the polymer size through the addition of maltose to the carbon source. A specific ratio of maltose acts to limit the chain length produced by the enzyme dextransucrase acting on sucrose. The IMOs in this work were produced by a sucrose to maltose ratio of 2:1. Syrup containing said fermentation products was obtained after ion exchange and chromatographic separation of the fermentation broth. Mannitol was then removed to produce isolated IMOs. The said mixture produced by this process was found to be readily catabolized by *Bifidobacteria* and *lactobacillus* but not readily utilized by either *Salmonella* sp., or *E. coli*, pointing towards its use in intestinal microflora modification. The said mixtures were non-competitive inhibitors of α-glucosidase (maltase), an enzyme required for starch or maltodextrin utilization, and decreased the abdominal fat in mammals.

EXAMPLE 1

Materials and Methods

Organism, Culture Medium, and Inoculum Preparation

All strains of bacteria used in this study were obtained from the American Type Culture Collection (ATCC, Manassas, Va.). They were maintained on agar slants, at 4° C. and transferred monthly. Anaerobes were subcultured weekly. *Salmonella typhimurium* (ATCC 14028) and *Escherichia coli* B (ATCC 23226) were maintained on tryptic soy agar (Difco, Detroit, Mich.). *Bifidobacterium bifidum* (ATCC 35914), *Bifidobacterium longum* (ATCC 15708), *Lactobacillus johnsonii* (ATCC 33200), and *Leuconostoc mesenteroides* (ATCC 13146) were maintained anaerobically on *Lactobaccilli* MRS slants (Difco, Detroit, Mich.) containing 0.05% (w/v) cysteine. Chicken ceca were kindly supplied by the Russell Research Center (USDA ARS, Russell Research Center, Athens, Ga.). Screening and isolation for chicken ceca bacteria were conducted following the method described by R. Hartemink et al., "Comparison of media for the detection of *Bifidobacteria, lactobacilli* and total anaerobes from fecal samples," J. Mircrobiol. Meth., vol. 36, pp. 181-192 (1999). Basically, ceca (from 6 weeks to 8 weeks broilers) in a plastic bag were homogenized by kneading the bag, and a subsample of about 10 g was transferred to a preweighed glass container containing 90 ml anaerobic buffered peptone water (Oxoid) with 0.5 g/L L-cysteine-HCl. The container was then closed and weighed to determine the actual sample size. Mixed samples were diluted further with reduced physiological salt solution ("Rps," peptone 1 g/L, L-cysteine-HCl 0.5 g/L and NaCl 8 g/L) or test media (MRSB; Difco). Finally, the samples were plated on the media and incubated at 37° C. for 48 h. Unless otherwise stated, mixing, diluting, plating and incubation were carried out anaerobically. Six colonies out of the hundreds were selected randomly and designated as chicken ceca isolates #1 to #6.

Preparation of Oligosaccharides

Batch fermentations were conducted in a 2-L BioFlo II fermentor (New Brunswick Scientific Co.) with a working volume of 1.0 L. The media had the following composition: sucrose (100 g/L); maltose (50 g/L); yeast extract (5 g/L); $MgSO_4.7H_2O$ (0.2 g/L); $FeSO_4.7H_2O$ (0.01 g/L); NaCl (0.01 g/L); $MnSO_4.7H_2O$ (0.01 g/L); $CaCl_2$ (0.05 g/L); $KH_2PO_4$ (3 g/L) with pH 7.2. Fermentors were inoculated from late log phase flask cultures at 1.0% of working volume. Fermentations were conducted at pH 6.5, 28° C., and 200 rpm. After harvesting, cells were removed by centrifugation at 10,400×g for 20 min (Dupont Sorvall RC5C, Newtown, Conn.). Activated charcoal (5 g/L, Sigma Chem. Co., St. Louis, Mo.) and Celite 545 (1 g/L, Fisher Scientific, Fair Lawn, N.J.) were added to cell-free culture broth and mixed at 50° C. for 20 min. The broths were then filtered through No. 6 filter paper (Whatman International Ltd., Maidstone, England) to remove the carbon. The filtered broths were desalted using ion-exchange columns filled with an anion-exchange resin in the hydroxide form and a cation-exchange resin in the hydrogen form (Rohm and Haas, Philadelphia, Pa.). The eluents were concentrated by vacuum evaporation (Brinkmann Instrument Inc., Westbury, N.Y.) to 65% solids. Mannitol crystallized upon cooling the concentrates, and was removed by decantation. Isomaltooligosaccharides were separated from the mannitol free concentrates using a cation exchange column (in calcium form); the isomaltooligosaccharide fractions were concentrated by vacuum evaporation.

Analytical Methods

Bacterial growth was measured by turbidimetry at 660 nm, calibrated against cell dry weight. Cells from a known volume were harvested by centrifugation at 10,400×g for 2 min (Dupont Sovall 24S, Newtown, Conn.), washed with deionized water, resuspended in a minimum volume of water, and dried (initially overnight at 95° C. and then at 105° C.) to constant weight. An absorbance of 1.0 at 660 nm was equivalent to 0.51 g of dry matter·liter$^{-1}$.

Thin Layer Chromatography (TLC)

Separation and qualitative identification of oligosaccharides was conducted using TLC. Whatman K6F silica gel plates of sizes (10×20 cm) were obtained from Fisher Scientific (Chicago, Ill.). A homologous series of isomaltodextrins (DP 1-10) was donated by Chonnam National Univ. (Kwangju, Korea). Maltopentaose, maltohexaose, maltoheptaose, panose, glucose, and isomaltotriose (Sigma Chem. Co., St. Louis, Mo.) and a commercial mixture of isomaltooligosaccharides (Wako Pure Chemical Industry Ltd., Osaka, Japan) were used as standards. Aliquots (1-2 μL) of the solutions to be analyzed were applied 20 mm from the bottom of the TLC plates with 10 μL micro syringe pipettes. The plates were developed at ambient temperature, using a mixture of solvents (acetonitrile, ethyl acetate, propanol, and water in volume (ml) at proportions of 85:20:50:70, respectively). After development was complete, the plates were dried, and the carbohydrates visualized using a spray of an ethanol solution containing 0.3% (w/v) α-naphthol and 5% (v/v) $H_2SO_4$. After air-drying, spots were developed by heating in an oven for 10 to 20 min at 100° C. Isomaltooligosaccharides were identified by comparing their chromatographic behavior with those of the standards.

Cation Column Chromatography

Different types of cation resins (Na, K, Ca form) were tested for separation of isomaltooligosaccharides from the end fermentation products. Resins (Duolite CR-1320, Rohm and Haas, Philadelphia, Pa.) in glass-jacketed columns (10 mm (Inner diameter)×100 mm (Length); working volume 70 ml) were regenerated using 5% solutions of NaCl, KCl, or CaCl. The temperature of the water eluent and the circulating water for glass jacket were 92 and 80° C., respectively. No pressure on the column was applied. Injection volume was 1 ml of solution (15 Brix° IMO). The detector was a differential refractometer (Waters).

High Performance Ion Chromatography

High-performance ion chromatography using a CarboPac MA1 column (Dionex, Sunnyvale, Calif.) and a pulsed amperometric detector (PAD, Dionex) was used for quantitative analysis of glucose, fructose, sucrose, mannitol, and maltose concentrations in solution. The samples were eluted at 0.4 ml·min$^{-1}$ with a 0.48 M NaOH solution. Oligosaccharide concentrations were calculated from peak areas of high-performance liquid chromatography on an Aminex-HPX-87K Bio-Rad column (Bio-Rad Lab. Hercules, Calif.) run at 85° C. with $K_2HPO_4$ as eluent, at a constant flow rate of 0.5 ml·min$^{-1}$, using glucose as a standard.

$^{13}C$ Nuclear Magnetic Resonance

The isomaltooligosaccharides (DP 1 to DP 8) were analyzed using a DPX 250 (63 MHz $^{13}C$) system with help of the Department of Chemistry, Louisiana State University (Baton Rouge, La.). The chemical shifts were expressed in ppm relative to the methyl signal of acetone in deuterium oxide solvent which was used as an internal standard at δ=29.92 ppm. The various signals were identified as described by F. Seymour et al., "Structural analysis of dextrans containing 4-O-α-D-glucosylated α-D-glucopyranosyl residues at the branch points, by use of 13C-nuclear magnetic resonance spectroscopy and gas-liquid chromatography-mass spectrometry," Carbohydr. Res., vol. 75, pp. 275 (1979); and M. Remaud et al., "Characterization of α-1,3 branched oligosaccharides synthesized by acceptor reaction with the extracellular glucosyltransferases from L. mesenteriodes NRRL B-742," J. Carbohyd. Chem., vol. 11, pp. 359-378 (1992).

Kinetic Assay for α-glucosidase

α-Glucosidase (maltase; EC 3.2.1.20), β-NAD, glucose dehydrogenase (EC 1.1.147) and other reagent chemicals were obtained from the Sigma Chemical Co. (St. Louis, Mo.). The kinetic assays were based on the following reaction;

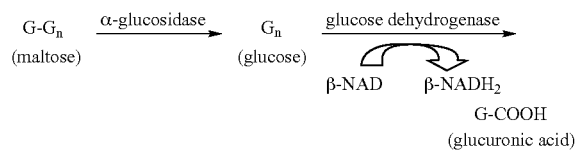

The kinetic assays were all performed in 96-well plates and read at wavelength 320 nm in a SPECTRAmax Plus microtiter plate reader (Molecular Devices Corp., Sunnyvale, Calif.) at 37° C. The software package Softmax™ was used for data analysis. α-Glucosidase (maltase; EC 3.2.1.20), β-NAD, and glucose dehydrogenase (EC 1.1.147) solutions were prepared with 0.1M $K_2HPO_4$ (pH 7) buffer. Each well contained 25 μl of 0.13 IU/ml glucose dehydrogenase, 25 μl of 1.65 IU/ml of α-glucosidase, and 20 1l of 12 mM of β-NAD in a total volume of 200 μl with different combinations of sugars and 0.1M $K_2HPO_4$ (pH 7) buffer. Absorbance change with time was measured at 320 nm.

Oligosaccharide Utilization by Selected Microorganisms

The growth of selected bacteria in the presence of isomaltooligosaccharides was compared by measuring absorbance over time at 660 nm. The media used for both the Bifidobacteria sp. and L. johnsonii was of the same composition as Lactobacillus MRS broth with 0.05% (w/v) cysteine, except the carbon source was replaced by various oligosaccharide preparations. The growth media for S. typhimurium and E. coli was tryptic soy broth, with the carbon source replaced by purified isomaltooligosaccharides. Carbon sources were supplied at a final concentration of 0.5% (w/v). All carbon sources were filter sterilized (0.2 μm). The following carbon sources were compared: glucose (Sigma Chem Co., St. Louis, Mo.), commercial fructooligosaccharides (FOS; >97.5%, Samyang Genex Co., Seoul, Korea), and isomaltooligosaccharide preparations. Individual culture, anaerobic growth tests were conducted in sealed glass test tubes. Each tube was inoculated from an overnight culture with either S. typhimurium or E. coli and a 24 to 48 hr culture of a Bifidobacteria sp. or L. johnsonii. The experiments with Bifidobacteria sp. and L. johnsonii were conducted under anaerobic conditions using anaerobic jars (BBL Microbiology Sys., Cockeysville, Md.) or the Oxyrase plate system (Oxyrase, Inc., Mansfield, Ohio). MRS broth containing 0.05% (w/v) cysteine with oligosaccharides as a carbon source was used for mixed cultures of S. typhimurium and L. johnsonii. Total viable counts were conducted on MRS agar and the cell numbers of S. typhimurium were determined from growth on MacConkey agar plates (Difco, Detroit, Mich.). The cell numbers for L. johnsonii were obtained as the difference between total viable count and S. typhimurium numbers. TLC was used to determine oligosaccharide consumption patterns of various strains. The media was MRSB (Difco) for Bifidobacteria and ceca bacteria, and TSB (Difco) for S. typhimurium and E. coli containing 0.5% (w/v) of Leuconostoc isomaltooligosaccharides instead of glucose as the carbon source. Media pH was adjusted to 6.0 and 0.1% (v/v) inoculum grown overnight in MRSB was used. During the growth, samples were taken at various times. Samples (2 μl) were applied on TLC plates.

EXAMPLE 2

Oligosaccharide Production

Isomaltooligosaccharide (IMO) Production by Acceptor Reaction

Figure 2:
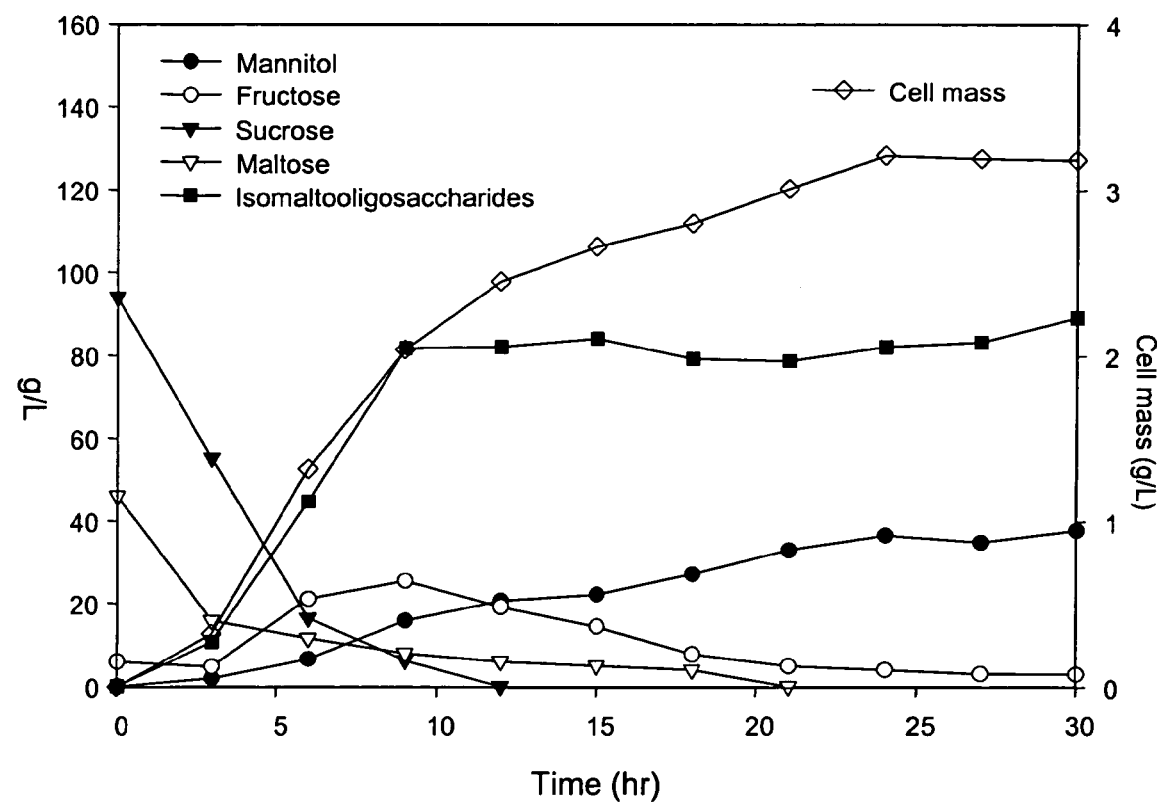
FIG. 2 illustrates the production of various isomaltooligosaccharides by *L. mesenteroides* ATCC 13146 from sucrose (10% w/v) and maltose (5% w/v) as a function of time.

IMO production by L. mesenteroides ATCC 13146 from sucrose (10% w/v) and maltose (5% w/v) was followed over time up to about 30 hr. As shown in FIG. 2, IMO production was complete by late log phase, about 10 hr post-inoculation, and levels did not drop thereafter. Sucrose disappeared rapidly during log phase of growth, with sucrose depletion corresponding to the transition point to stationary phase. Once sucrose was depleted, the accumulated fructose was metabolized to mannitol with a decrease in growth rate compared to growth on sucrose. Fructose concentration peaked about the end of log phase then decreased slowly. Mannitol production occurred through the lag phase to the stationary phase and was linked to the fructose concentration where the rate of fructose disappearance was the inverse of the rate of mannitol formation. Oligosaccharide production was associated with cell growth. The conversion of fructose to mannitol was associated with the accumulation of fructose. Upon completion of fermentation, the cell mass was 3.2 g/L. The weight % yield of oligosaccharide (product produced×100/[(160×mole of sucrose consumed)+(342× mole of maltose consumed)]) was 82% of theoretical, the number 160 in the equation from 342 (sucrose M.W.)−((180 (fructose M.W.)+2 (hydrogen M.W.)) and the conversion of fructose to mannitol was 71% of theoretical.

Thin layer chromatography (TLC) clearly showed the course of IMO production. (Data not shown). As fermentation proceeded, mono- and disaccharides disappeared as the higher DP (degree of polymerization) polysaccharides were formed. By 24 hr, all mono- and disaccharides had been converted to higher oligosaccharide polymers. Four main isomaltooligosaccharides were found. The sizes of these oligomers were compared with a commercial oligosaccharide product of known composition. The *Leuconostoc* isomaltooligosaccharides were branched polymers with a size range of DP 2 to 7.

The oligosaccharides, based on their linkages, showed different Rf values (Data not shown). The migration of branched isomaltodextrins containing single α-1,3 or α-1,4 linkages, was faster than equivalent dextrins containing only α-1,6 linkages, as indicated by J. F. Robyt et al., "Separation and quantitative determination of nanogram quantities of maltodextrins and isomaltodextrins by thin-layer chromatography," Carbohydr. Res., vol. 251, pp. 187-202 (1994). The migration of the *Leuconostoc* oligosaccharides was faster than equivalent isomaltodextrins (α-1,6 linkages), but slower than equivalent maltodextrins (α-1,4 linkages).

Oligosaccharide Separation

Figure 3:
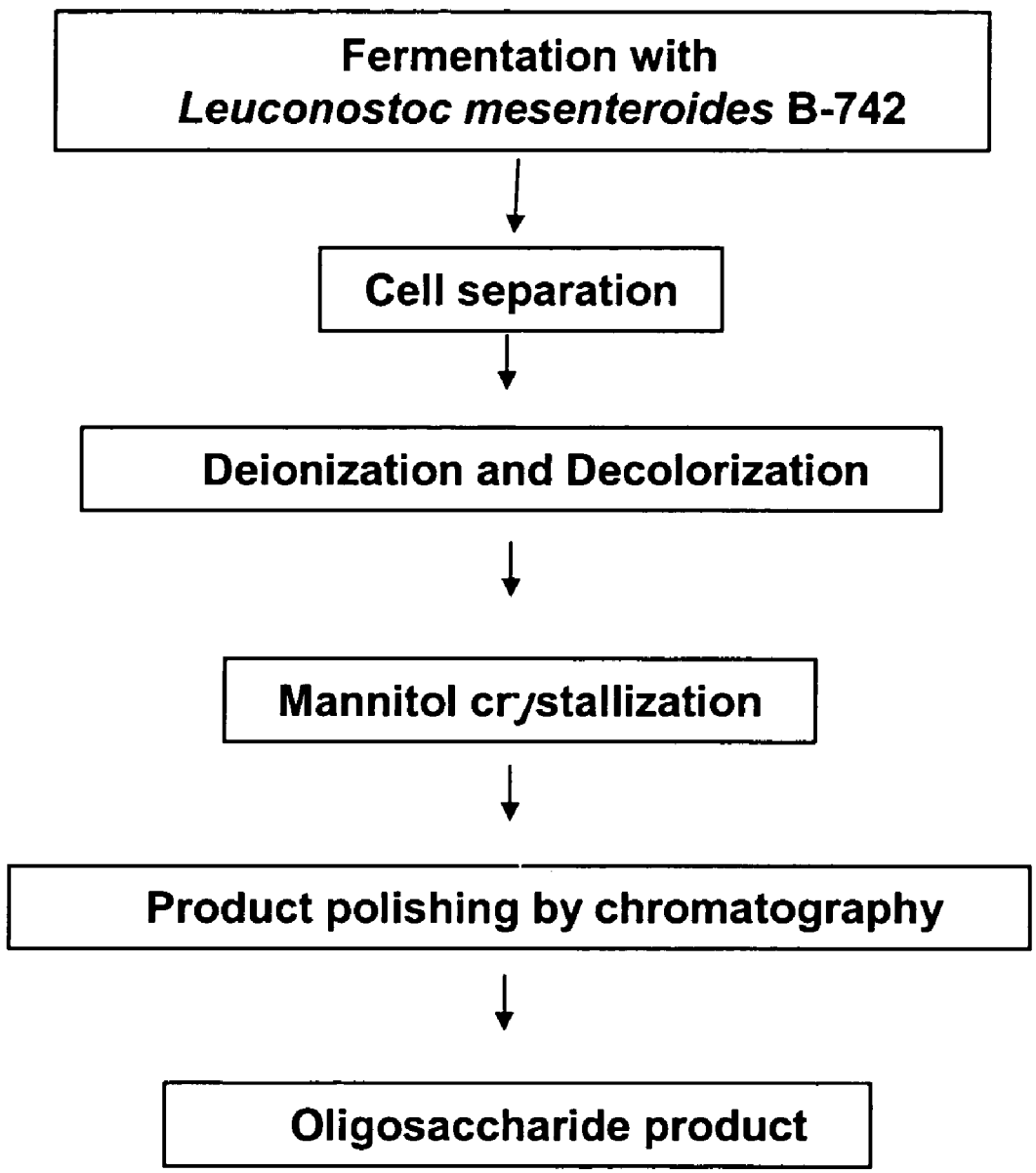
FIG. 3 illustrates the flow chart for the production of isomaltooligosaccharides as used in this study.

The fermentation broth, after cell separation, contained oligosaccharides, mannitol and some organic acids. Because the oligosaccharides are neutral polymers, and the other components (acids, color compounds and salts) are charged, cation resins were used for separation of oligosaccharides. Neither $K^+$ nor $H^+$ cation columns clearly separated the oligosaccharides from the mannitol and other products, whereas $Ca^{2+}$ cation columns produced two well separated peaks (Data not shown). When analyzed by HPLC as described above, the first peak contained all the isomaltooligosaccharides, and the second peak contained mannitol and organic acids, e.g., acetic acid and lactic acid (Data not shown). Based on these results, the process for producing an oligosaccharide product was developed as shown in FIG. 3.

Mannitol Separation

Crystallization at 4° C. separated most of the mannitol from oligosaccharides as shown by HPLC analysis of the product at different stages: the broth after deionization, the broth after mannitol crystallization (86.4% recovered); the mannitol product (>99.0% purity, calculated by the HPLC peak area); and the oligosaccharide product after the cation exchange ($Ca^{2+}$ form) column (>98.8% purity). (Data not shown) Pure oligosaccharide solution (14.5 Brix°) was concentrated to 60 Brix° by evaporation. The concentrated pure isomaltooligosaccharides (ca. 60% w/v) were used for the further testing. Table 2 shows the product yields at various stages of the production.

Mannitol was a major end product in the *Leuconostoc* fermentation. However, mannitol must be separated from the oligosaccharides if they are to be used as prebiotics, as mannitol can also be a carbon source for microorganisms. Most of the mannitol (86.4%) was recovered without further processing by crystallization at 4° C. To obtain highly purified oligosaccharides (>98.8%), a cation exchange column was used. A $Ca^{2+}$ resin has high ionic strength and divalent properties, which may account for the increased resolution seen when it was used. On a $Ca^{2+}$ resin, the oligosaccharides eluted first followed by a mixture of mannitol and organic acids (lactic acid and acetic acid). The smaller mannitol molecule eluted after the oligosaccharides in part because of partial ionization of the mannitol at the 6.5 pH. Divalent cations such as $Ca^{2+}$ bind strongly to the organic acids. At pH 6.5, which is above the pK value of lactic and acetic acids, they exist in dissociated forms. The stronger organic acid that is lactic (pK of 3.79) eluted later because it interacts more strongly with $Ca^{2+}$ than acetic acid, pK value of 4.7.

TABLE 2

Product yields and process for production of glucooligosaccharides

| Process | Components in process | | |
|---|---|---|---|
| Fermentation | Input | Sucrose (10% w/v) | 100 g/L |
| | | Maltose (5% w/v) | 50 g/L |
| | | Yeast extract and salts | 8.28 g/L |
| | ⇩ | | |
| | Output | Oligosaccharides | 80.1 g/L (82.3%[a]) |
| | | Mannitol | 37.6 g/L (70.1%[b]) |
| | | Acids, ethanol and cell mass | 5.75 g/L |
| Decolorization and deionization | ⇩ | | Removal of color pigments and salts |
| Evaporation | | | Concentrated to ca. 60% (w/v) |
| Crystallization | | | at 4° C. |
| | Oligosaccharides, residual mannitol | | Mannitol (86.4% recovered, 99.0% purity) |
| $Ca^{2+}$ Ion exchange | ⇩ | | |
| | Purified oligosaccharides | | 98.8% purity |

[a] Weight % yield of oligosaccharide (product produced × 100/[(160 × mole of sucrose consumed) + (342 × mole of maltose consumed)])
[b] % fructose conversion to mannitol

EXAMPLE 3

Composition and Structure of Isomaltooligosaccharide Products

Figure 4:
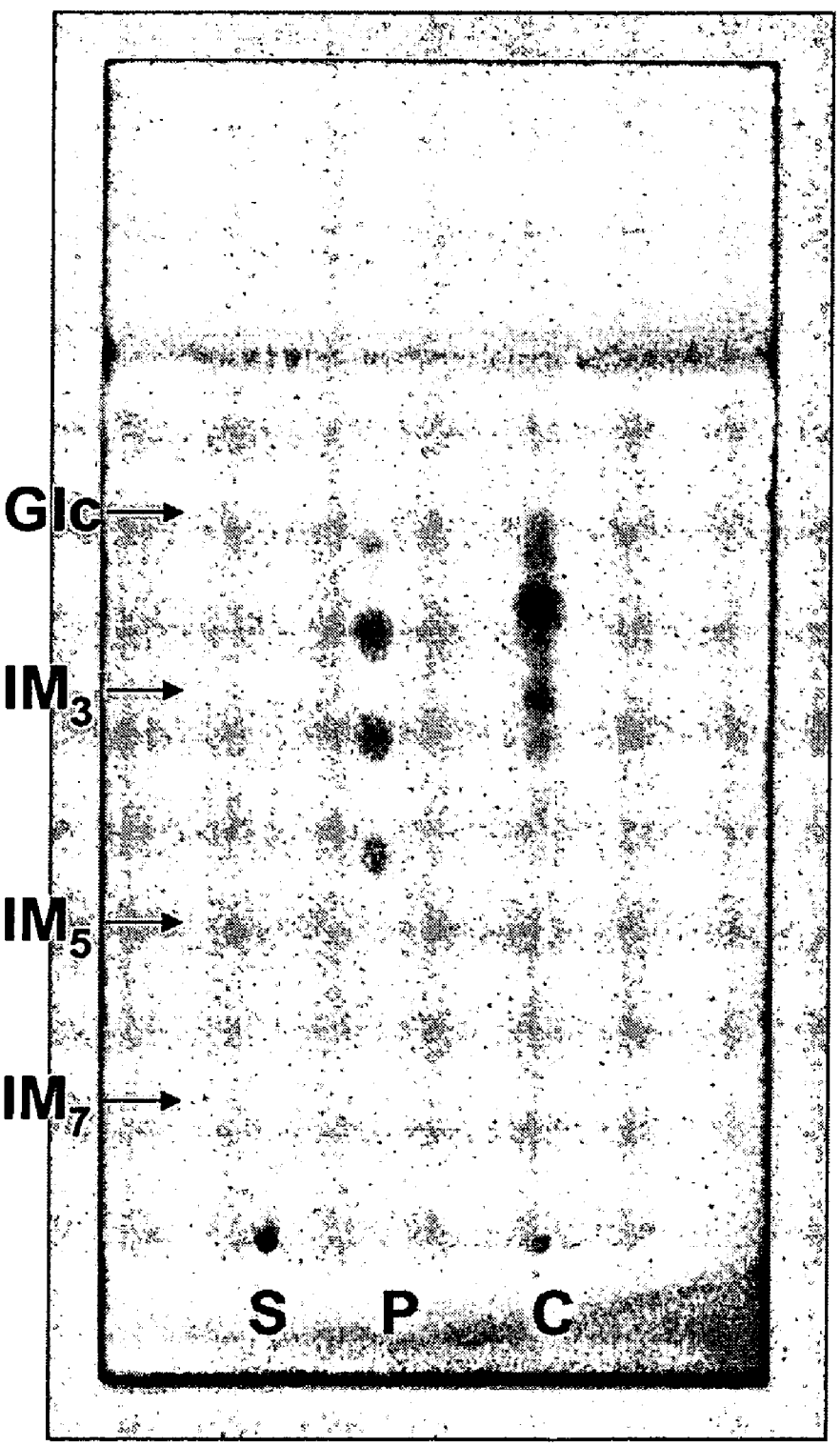
FIG. 4 illustrates the results of thin layer chromatography indicating the types of branched α-isomaltooligosaccharides of *L. mesenteroides* (ATCC 13146). The abbreviations used are as follows: S, Isomaltodextrins; P, Isomaltooligosaccharide product; C, Commercial isomaltooligosaccharides (Wako Pure Chemical Industry Ltd., Osaka, Japan); Glc, glucose; $IM_3$, Isomaltotriose; $IM_5$, Isomaltopentaose; and $IM_7$, Isomaltoheptaose.

Thin layer chromatography (as described in Example 1) showed that IMO were branched polymers ranging in size from DP 2 to 7 (FIG. 4). By HPLC peak area, there was 6.9% DP 2, 28.4% panose, 36.7% branched DP 4, 19.1% branched DP5, 7.4% branched DP6, and 1.2% branched DP7. In the pure form, there was only a trace amount of monosaccharides (<0.2%) present, and no polysaccharides larger than DP 7.

Figure 5:
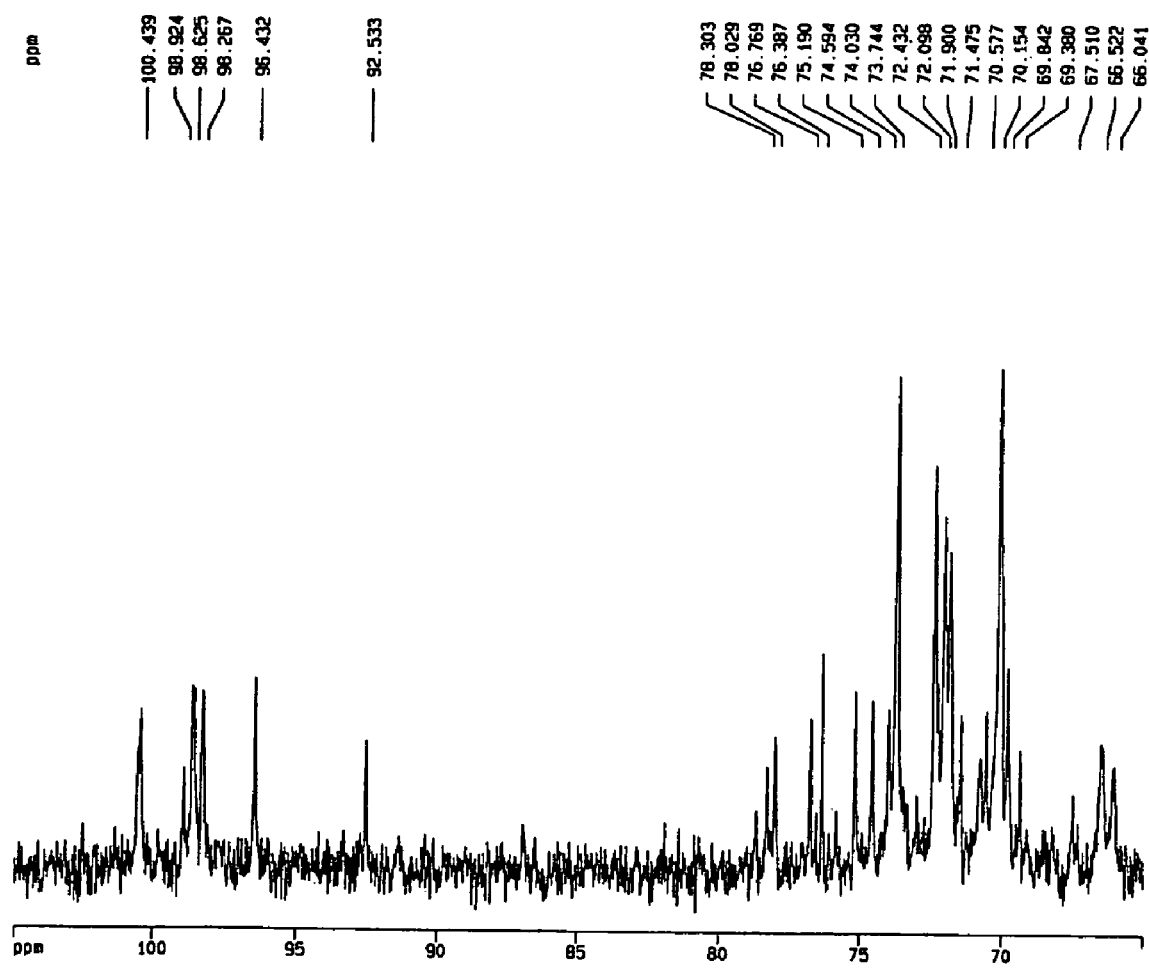
FIG. 5 illustrates the results of $^{13}C$ NMR of the branched α-isomaltooligosaccharides of *L. mesenteroides* (ATCC 13146).

Structural analysis of IMOs by $C^{13}$ NMR (as described in Example 1) showed that the IMOs are linked mainly by α-1,4 and α-1,6 linkages (FIG. 5). These oligosaccharides were analyzed using a DPX 250 (63 MHz $^3$C) system. The chemical shifts in FIG. 5 are expressed in ppm relative to the methyl signal of acetone in a deuterium oxide solvent, which was used as an internal standard at δ=29.92 ppm. The various signals were assigned as described by Seymour et al. (1976) and Remaud et al. (1992): 85-105 ppm, the anomeric region (mainly 97-103 ppm, as there is only an infinitesimal proportion of reducing sugar in any of the polymers); 70-75 ppm, C-2,3,4 and 5; 60-70 ppm, bonded and non-bonded C-6 atoms; 75-85 ppm, signals of bonded C-2, C-3, C-4, C-5.

Two closely separated peaks at 100.44 ppm were also encountered in the spectrum of maltose, and both correspond to a glucose molecule linked to a reducing residue of maltose by an α-1,4 linkage (See Remaud et al., 1992). This also implied that the α-1,4 linkage is located at the reducing end of isomaltosyl residues containing α-1,6 linkages. The peaks corresponding to the region of 98.0-99.0 ppm showed α-1,6 linked residues. However, the intensity of the resonances for α-1,3 bonds around 100.0 and 80.6-81.2 ppm were not present (Dols et al., 1998; Remaud et al., 1992).

The isomaltooligosaccharides produced were branched polymers between DP 2 and 7 in size. Prior researchers had reported that the oligosaccharides synthesized by the dextransucrase from this bacterium had α-1,6 backbones with α-1,3, and/or α-1,4-branched side chains when maltose was used as an acceptor. See Remaud et al. (1992). However, under the current conditions, the IMOs produced contained mainly α-1,4 and α-1,6 linkages and maltose was linked to the reducing end of the isomaltosyl residues.

EXAMPLE 4

Isomaltooligosaccharides as Microbial Growth Modifiers
Individual Cultures
Growth of selected bacteria on L. mesenteroides ATCC 13146 isomaltooligosaccharides as a carbon source was compared with growth on a commercial fructooligosaccharide (FOS) mixture. Both types of oligosaccharides produced significantly reduced growth of S. typhimurium and E. coli compared with growth on glucose (Table 3). Based on the TLC analysis of the medium at different times, these organisms could not use the IMOs efficiently (Data not shown). There was no significant difference between growth rates on either of the oligosaccharide preparations. The growth rate suppression of E. coli in the presence of IMOs was marginally greater than that of S. typhimurium (Table 3). The growth of selected probiotic strains on IMOs was also compared. Leuconostoc IMO supported the growth of Bifidobacterium longum and L. johnsonii and showed no significant difference when compared to glucose as carbon source. B. longum degraded almost all components of the IMO within 24 hrs as shown by TLC (Data not shown). Utilization of the IMO product by B. bifidium was less rapid (74.9% relative to growth rate of FOS) than utilization of a commercial FOS and glucose. This Vindicates that the growth of probiotic strains was also dependent on the type of oligosaccharides.

TABLE 3

Growth comparison on isomaltooligosaccharide preparations: IMO, Leuconostoc isomaltooligosaccharides; FOS, Commercial fructooligosaccharides (Samyang Genex Co., Seoul, Korea)

| Organism | Growth rate in exponential growth phase ([Absorbance unit × 100] · hr$^{-1}$) | | | Growth rate (on IMO/glucose) |
| --- | --- | --- | --- | --- |
|  | glucose | IMO | FOS |  |
| S. typhimurium | 9.89 | 3.64 | 3.48 | 36.8 |
| E. coli | 9.35 | 2.68 | 2.44 | 28.7 |
| B. bifidium | 13.30 | 9.81 | 13.10 | 73.8 |
| L. johnsonii | 11.06 | 10.74 | 10.70 | 97.1 |
| B. longum | 11.72 | 11.69 | 11.70 | 99.7 |

Figure 6:
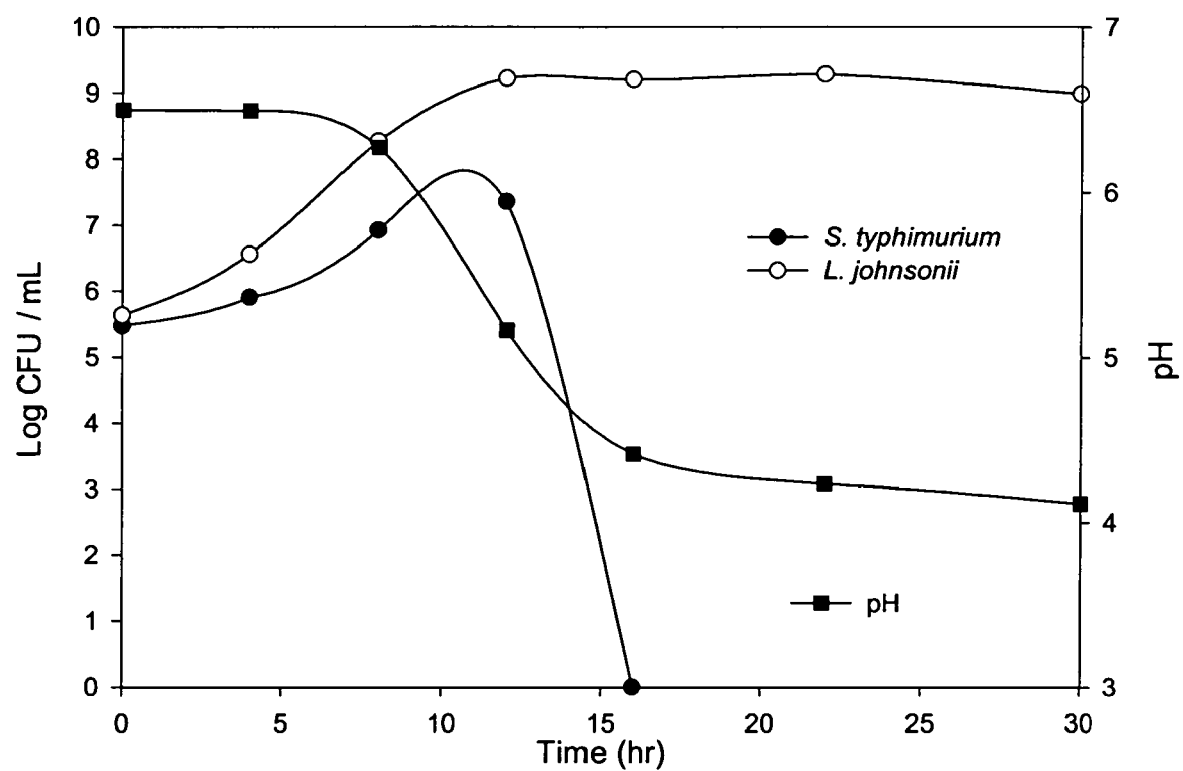
FIG. 6 illustrates the anaerobic growth of mixed cultures of *Salmonella typhimurium* and *Lactobacilli johnsonii* on the branched α-isomaltooligosaccharides of *L. mesenteroides* (ATCC 13146) preparation at 37° C.

Mixed Cultures
To test for prebiotic effects of the IMO, mixed cultures of S. typhimurium and L. johnsonii were grown on the oligosaccharides. FIG. 6 shows the anaerobic growth of the two mixed cultures over 30 hr, as a function of time and medium pH. When the medium pH was above 5.0, both organisms grew; however, S. typhimurium grew more slowly than L. johnsonii. As the population of L. johnsonii increased, the pH dropped. When the pH dropped below 5.0, S. typhimurium populations decreased until they were below detection level (<1).

When S. typhimurium or E. coli was grown on ATCC 13146 IMO preparations, there was less than 37% of the equivalent growth on glucose, similar to growth on commercial fructooligosaccharides (less than 35%). The fact that these bacteria showed similar growth on IMO and on FOS is surprising based on the literature. Lactobacillus johnsonii and B. longum showed no differences in growth rate on glucose or the IMO preparations. When L. johnsonii and S. typhimurium were grown together on oligosaccharide preparations, the oligomers stimulated the growth of the Lactobacillus, but were not readily utilized by the Salmonella. TLC showed clearly that the IMOs preferentially stimulated the growth of Bifidobacterium, but were not readily utilized by Salmonella and E. coli. It appears that these IMOs are selectively favored by some probiotic strains.

EXAMPLE 5

Utilization of IMOs by Bacteria Isolated from Chicken Ceca
Utilization of Leuconostoc IMOs by six bacterial isolates (all showed Gram positive, catalase negative and lactic acid formation from glucose) from chicken ceca was compared to utilization of a commercial fructooligosaccharide (FOS). Three of the six bacteria showed more growth after 24 hr on IMOs than on FOS (Table 4). In mixed cultures of bacteria from chicken ceca, the cecal bacterial isolates #5 and #6 showed the same use pattern of IMOs. Only the DP 3 polymer (panose) was utilized in the first 24 hours as shown by TLC (Data not shown).

TABLE 4

Growth comparison of chicken cecal bacteria on various substrates: glucose, IMO, Leuconostoc isomaltooligosaccharide; and FOS, Commercial fructooligosaccharides (Samyang Genex Co., Seoul, Korea)

| Organism | Relative growth to glucose as a carbon source at 24 hr incubation ([Absorbance unit of Glc at 24 hr/ Absorbance unit of x 100] · hr$^{-1}$) | | |
| --- | --- | --- | --- |
|  | glucose | IMO | FOS |
| C.B. #1 | 100.00 | 22.77 | 61.20 |
| C.B. #2 | 100.00 | 99.34 | 79.29 |
| C.B. #3 | 100.00 | 75.85 | 48.01 |
| C.B. #4 | 100.00 | 36.72 | 61.40 |
| C.B. #5 | 100.00 | 87.23 | 50.25 |
| C.B. #6 | 100.00 | 87.17 | 87.66 |

[a]Growth level at stationary phase (at 24 hr) on glucose was calculated as 100.
C.B.; Cecal Bacterium To test the potential of this IMO as a prebiotic in poultry, six different microbial strains were isolated from chicken ceca. These isolates were identified as lactic acid bacteria by colonial morphology and chemical reaction (Gram positive, catalase negative, and lactic acid formation from glucose, data not shown). When utilization of the Leuconostoc isomaltooligosaccharides by these isolates was compared with utilization of a commercially available fructooligosaccharide (FOS), surprisingly three of the six isolates showed better growth after 24 hr on IMO than on FOS. In tests of mixed cultures of these lactic acid bacteria and Salmonella on the IMOs, five of the six cecal isolates showed higher growth rates and inhibited the growth of Salmonella. Similar results were seen with Lactobacillus and Bifidobacterium strains. Two isolates showed identical patterns of consumption of IMO. They only degraded the DP 3 component of the IMO mixture. Similar effects have been seen in studies on the effect of fructooligosaccharides in feed trials with broilers where FOS reduced susceptibility of poultry to *Salmonella* colonization, increased *Bifidobacterium* levels, and reduced the level of *Salmonella* present in the caecum. See Bailey et al. (1991); and Chamber et al. (1997).

The low pH produced by the chicken cecal bacteria is likely responsible for the observed suppression of *S. typhimurium* growth in mixed cultures. Although other antagonistic substances such as bacteroicins and hydrogen peroxide could be produced that can inhibit *S. typhimurium*, significant levels of lactic acid bacteria must be generated first. These studies did not directly measure in vivo effects of IMO as produced in this study, but indicated that this IMO composition can be effective as an avian prebiotic.

EXAMPLE 6

Inhibition of α-glucosidase by IMOs
α-glucosidase and IMO

Figure 7:
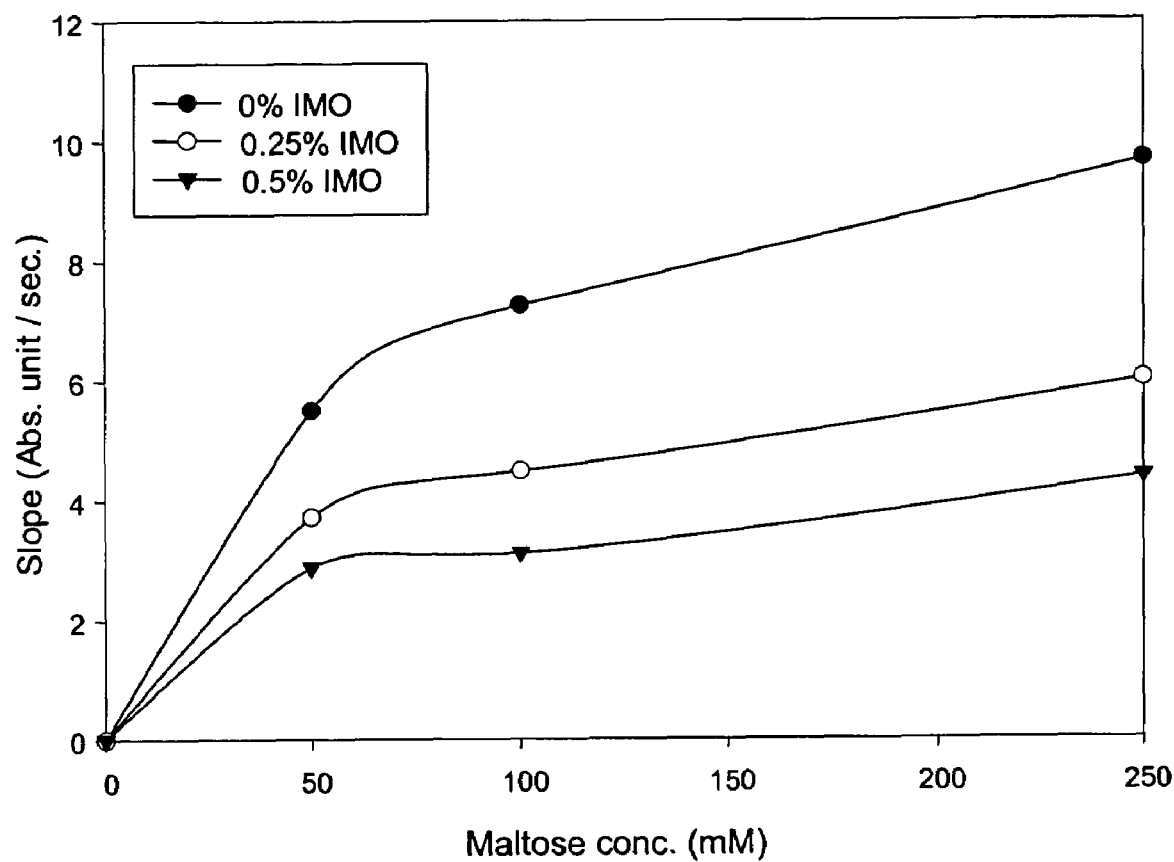
FIG. 7 illustrates the α-glucosidase (maltase) activity inhibition with increasing concentrations of the branched α-isomaltooligosaccharides of *L. mesenteroides* (ATCC 13146).
Figure 8:
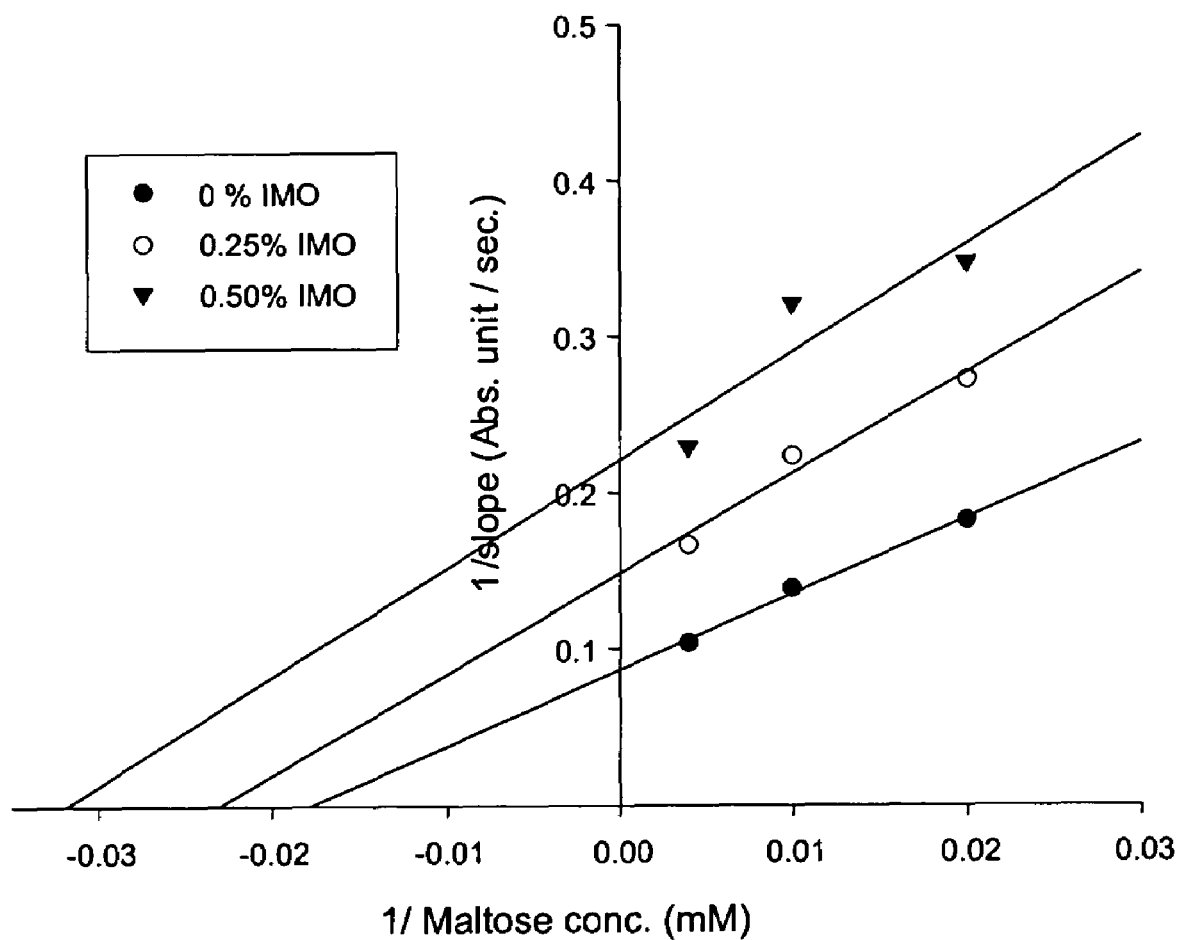
FIG. 8 illustrates a double reciprocal plot of α-glucosidase (maltase) activity inhibition as the concentration of the branched α-isomaltooligosaccharides of *L. mesenteroides* (ATCC 13146) increased.

The *Leuconostoc* IMO was found to inhibit the activity of α-glucosidase (maltase). FIG. 7 shows the inhibition of α-glucosidase activity with increasing concentrations of IMO (0%, 0.25%, and 0.5%) as measured at various concentrations of maltose (0, 50, 100, 250 mM). A double reciprocal plot of this data indicated this was a non-competitive inhibition (FIG. 8).

Figure 9A:
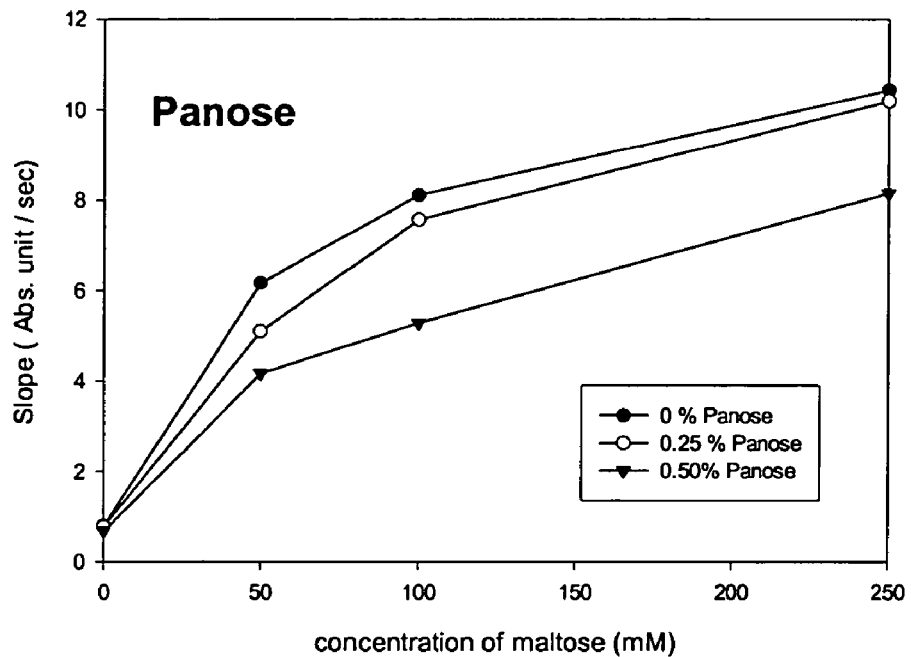
FIG. 9A illustrates the α-glucosidase (maltase) activity in the presence of different concentrations of panose (branched; α-1,4 and α-1,6).
Figure 9B:
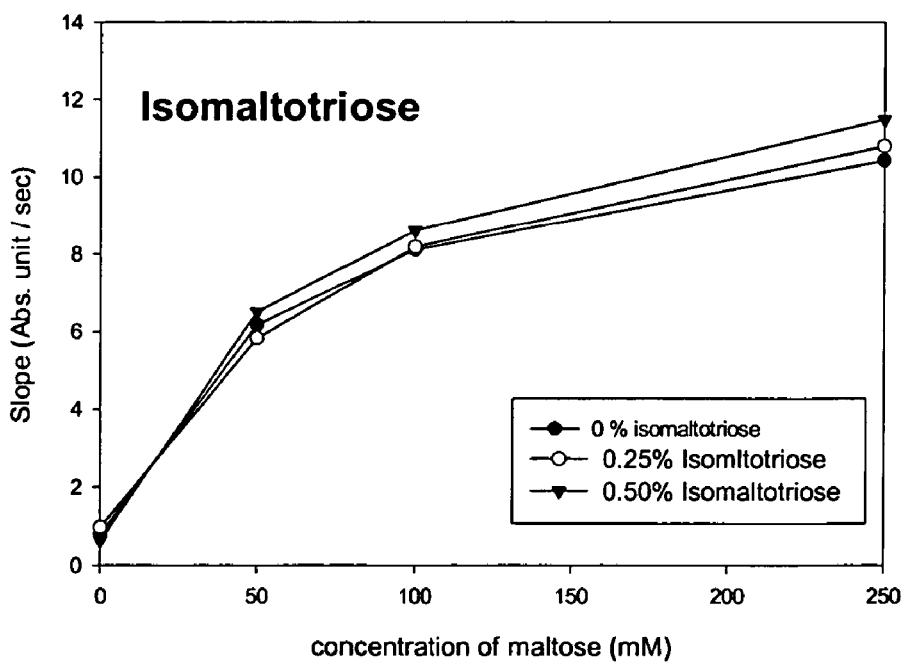
FIG. 9B illustrates the α-glucosidase (maltase) activity in the presence of different concentrations of isomaltotriose (linear; two α-1,6).
Figure 10A:
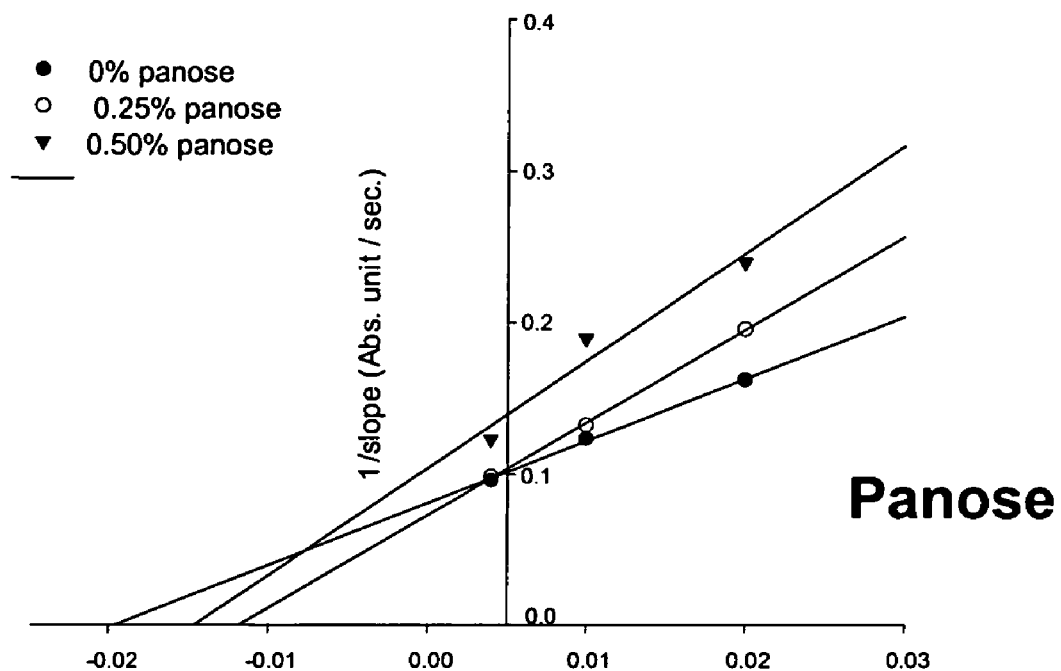
FIG. 10A illustrates a double reciprocal plot of α-glucosidase (maltase) activity inhibition as the concentration of panose (branched; α-1,4 and α-1,6) increased.
Figure 10B:
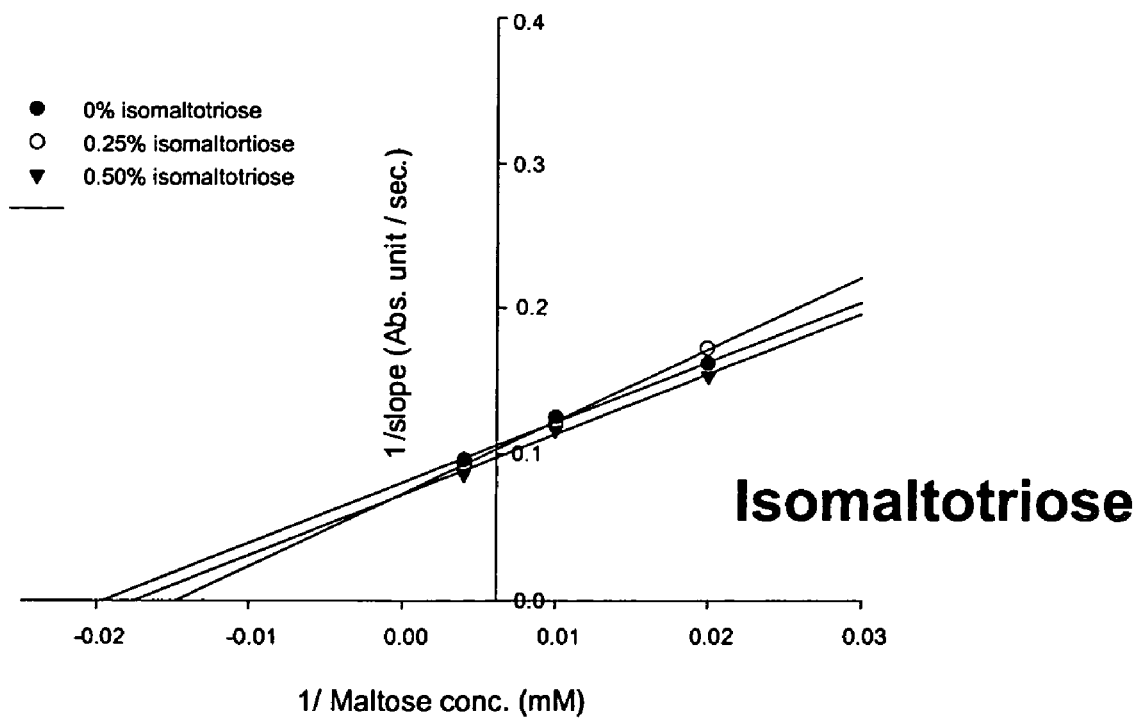
FIG. 10B illustrates a double reciprocal plot of α-glucosidase (maltase) activity inhibition as the concentration of isomaltotriose (linear; two α-1,6) increased.

In order to determine the role of branching in the inhibition, the Ki values for panose and isomaltotriose were also determined. FIGS. 9A and 9B shows the inhibition of α-glucosidase activity with increasing concentration of panose and isomaltotriose, respectively (0%, 0.25%, and 0.5%), as measured at various concentrations of maltose (0, 50, 100, 250 mM). A double reciprocal plot of this data is shown in FIGS. 10A and 10B. Only panose, containing α-1,4 and α-1,6 linkages, showed an inhibition on α-glucosidase. Isomaltotriose, a linear glucose polymer linked by two α-(1→6) linkages, was not inhibitory.

Growth Test of *B. longum* and *S. typhimurium* with Panose and Maltodextrins

Figure 11A:
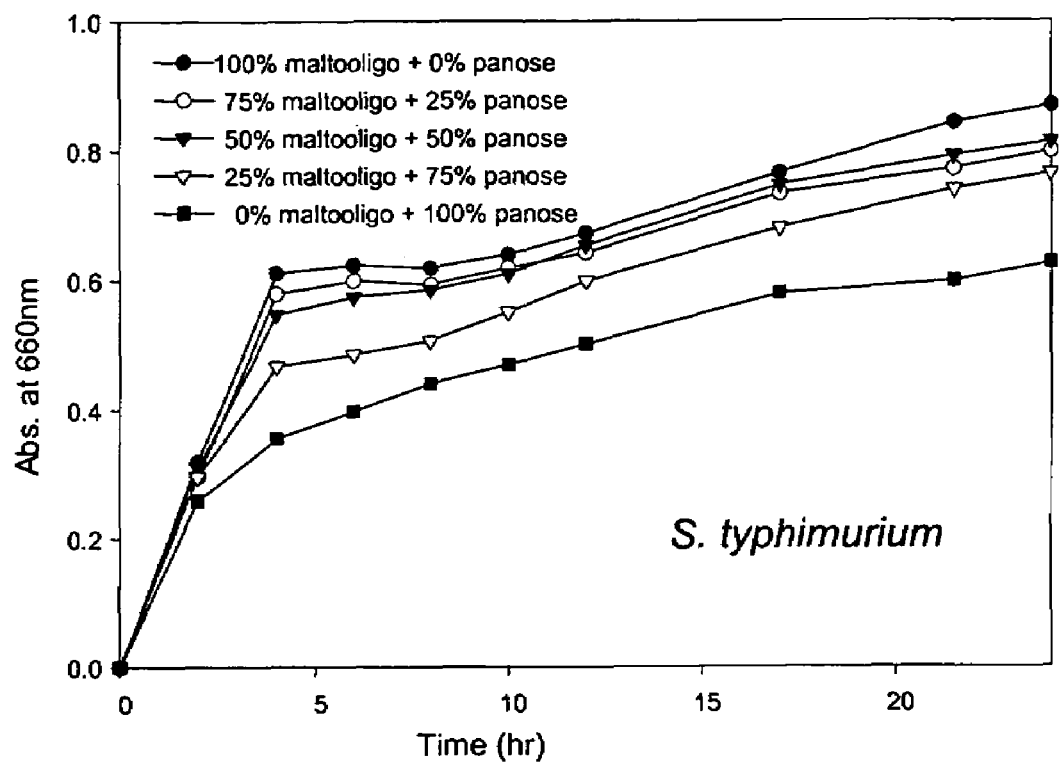
FIG. 11A illustrates the anaerobic growth of *Salmonella typhimurium* and *Bifidobacterium longum* on different combinations of panose (branched; α-1,4 and α-1,6) at 37° C.
Figure 11B:
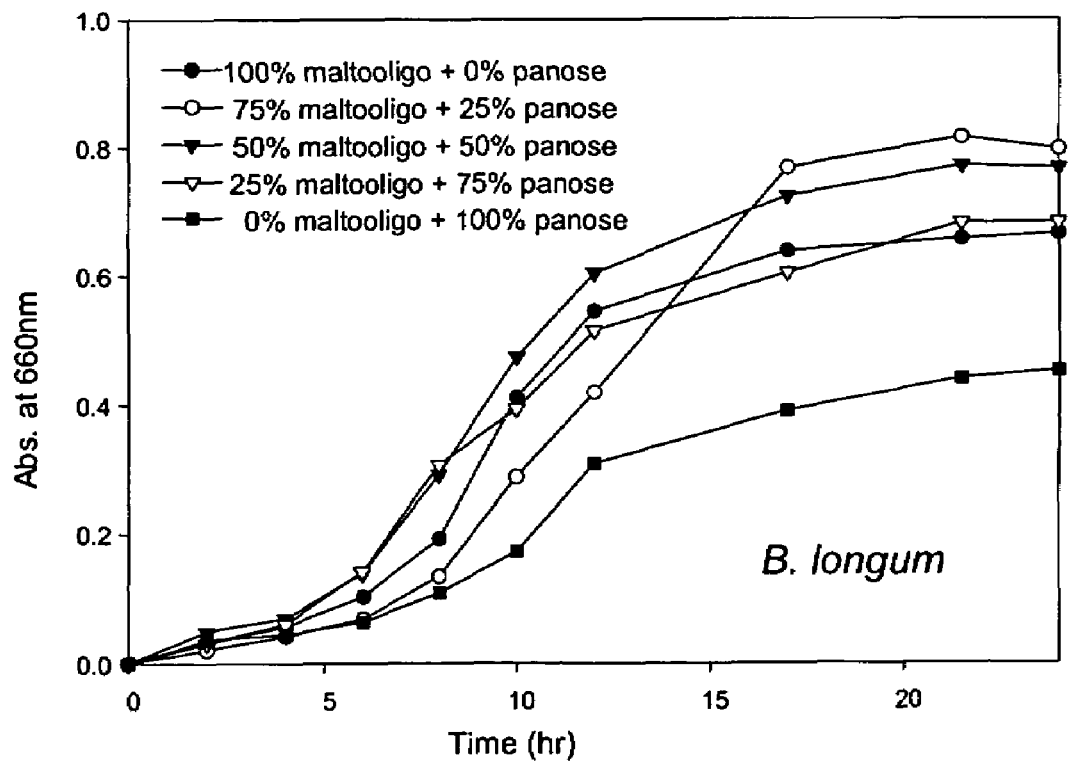
FIG. 11B illustrates the anaerobic growth of *Salmonella typhimurium* and *Bifidobacterium longum* on different combinations of maltooligosaccharides (d.p. 4-10) at 37° C.
Figure 12:
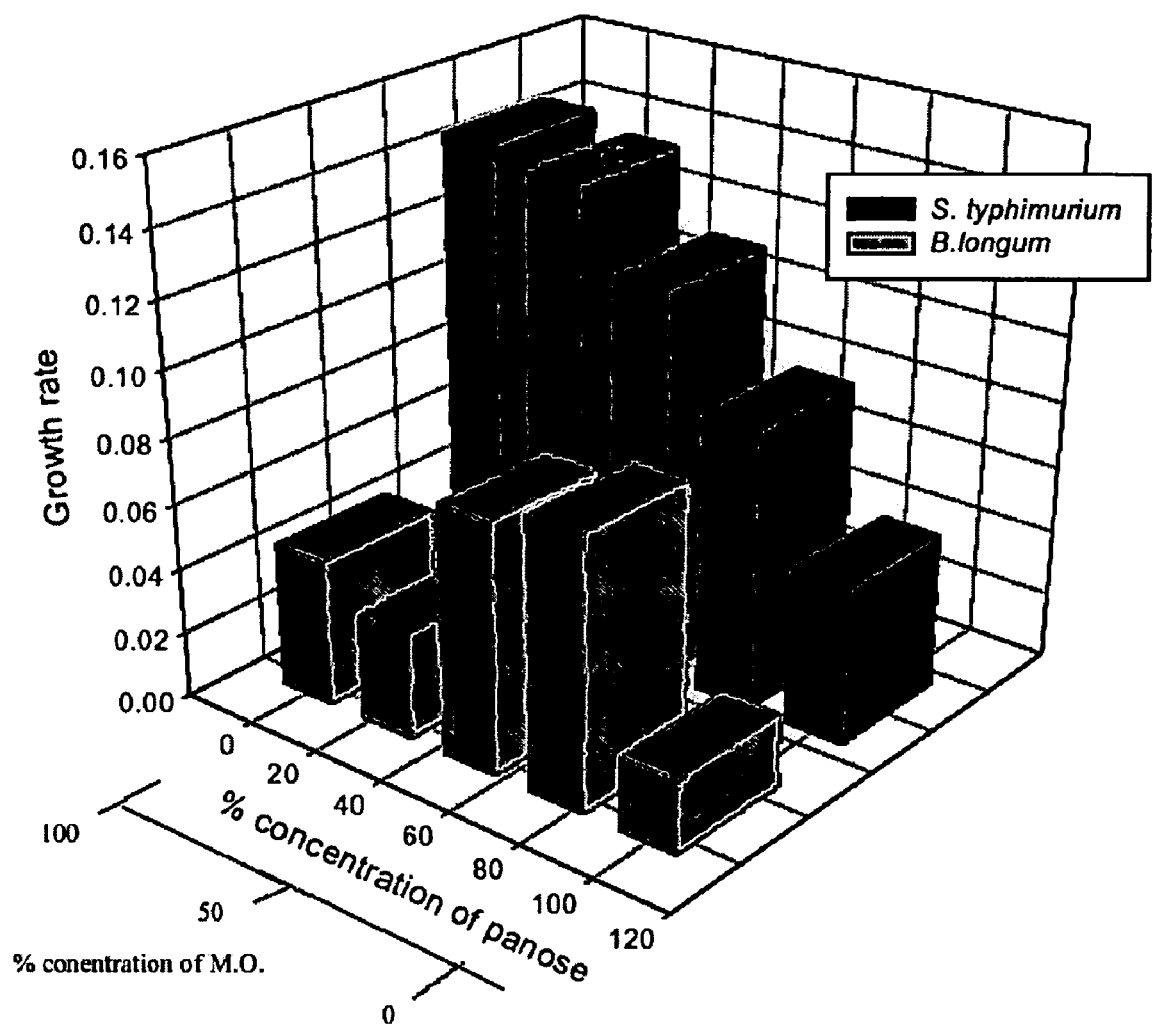
FIG. 12 illustrates a comparison of growth rates in log phase between *Salmonella typhimurium* and *Bifidobacte-*

To further determine whether *Leuconostoc* IMO acts as a starch-metabolism inhibitor, *B. longum* and *S. typhimurium* were grown in different combinations of panose and maltooligosaccharides (from DP 4 to DP 10). As the concentration of panose in the growth medium increased, the growth of *S. typhimurium* slowed but *B. longum* growth increased. (FIGS. 11A and 11B, respectively). A comparison of growth rates at log phase clearly showed the growth inhibition of *S. typhimurium* by panose (FIG. 12). In the case of *B. longum*, 50% panose+50% maltooligosaccharides and 75% panose+25% maltooligosaccharides combinations showed better growth than other combinations.

*L. mesenteroides* ATCC 13146 IMOs were found be a non-competitive inhibitor of α-glucosidase (maltase). To verify inhibition of α-glycosidase by branched oligomers, panose and isomaltotriose were tested for inhibition. Panose contains α-1,4 and α-1,6 linkages and is one of the components in the *Leuconostoc* IMOs. Panose inhibited α-glucosidase, whereas isomaltotriose, containing two α-1,6 linkages in a linear structure, did not. Panose also suppressed growth of *S. typhimurium* but not *B. longum*. *B. longum* showed increased growth when panose and maltodextrins were supplied in the medium together compared with maltodextrin alone. When growth rates at early log phase were compared, growth inhibition of *S. typhimurium* by panose was clearly evident.

Isomaltooligosaccharides (branched or partially branched) most likely inhibit some of those enzymes required for utilization of starch in other genera, such as *Escherichia* and *Salmonella*. Panose and the *Leuconostoc* isomaltooligosaccharides reduced the activity of α-glucosidase that degrades α-1,4 linkages in a maltose or maltodextrin. Panose alone did not produce a higher growth rate than maltooligosaccharides and panose together for *B. longum*. It is likely that high concentrations of panose also can inhibit enzymes seen in maltooligosaccharide inhibition. There seems to be a synergistic effect for the probiotic strains on carbon source utilization when maltodextrin and prebiotic sugars are present together.

EXAMPLE 7

Isomaltooligosaccharides as Dietary Supplement for Chicks Inoculated with *Salmonella*

Young chickens were used to test the effectiveness of these branched isomaltooligosaccharides (IMO) produced as described in Example 2 as a dietary supplement to reduce *Salmonella* intestinal infections. Young chickens (commercial Leghorn broiler chickens on day of hatch) were orally inoculated with *Salmonella* using a round tip cannula attached to a syringe containing nalidixic acid-resistant *Salmonella*. This unique strain was used to be able to distinguish these bacteria from the general population. The chickens were then divided into four groups to be fed standard chicken feed (prepared and milled by the poultry department of the University of Georgia) with added concentrations of IMOs of 0, 1, 2 and 4% (w/w). On day 21, the chickens were sacrificed to examine the ceca (large intestine) and count the bacterial populations of *Salmonella*, *Bifidobacteria*, *Lactobacillus*, and total anaerobic bacteria. In addition, the weight gain efficiency was determined, and the general condition of the birds noted. There was no significant difference in weight gain efficiency between chickens fed IMO in the feed and control. There was a 0.1 pH unit drop in cecal pH in the birds receiving IMO at all concentrations.

Based on the above data (Examples 4 and 5) and the drop in pH, it is predicted that the IMO-supplemented food will be effective as a prebiotic, i.e., will increase the numbers of beneficial bacteria (*Bifidobacteria* and *Lactobacillus*) and decrease the numbers of pathogenic bacteria (*Salmonella*). Thus IMO-supplemented food would be useful as an antibiotic for poultry.

EXAMPLE 8

Toxicity Study of Isomaltooligosaccharides

To test whether the isomaltooligosaccharide composition produced as described in Example 2 is toxic to mammals, young rats were used and various body organs assayed after several weeks of feeding IMO-supplemented food. Young male Sprague-Dawley rats (about 2 months old, mean weight of 270 g) were used. The rats were divided into four groups of 5 to 6 rats per group. One group (the control) was fed standard rat chow (Purina rat chow). The other three groups were fed IMO-supplemented rat chow at a concentration of 5%, 10%, and 20%, respectively. The food intake and weight gain was measured twice a week for six weeks. At the end of six weeks, the rats were sacrificed to examine the weights of the major organs.

There were no significant differences in food intake (although a trend toward an increase in the IMO food intake was seen; p<0.058). Weight gain, heart weight, spleen weight, kidney weight, lung weight, brown adipose tissue weight, and white adipose tissue weight were determined. (Data not shown) There were significant differences in the weight of the caecum with an increased weight measured especially in the 10% and 20% IMO groups. This probably indicates an increase in the population of fermentation bacteria. Blood was also taken for future analysis.

There was also a significant effect of the IMO concentration on the abdominal fat gain when normalized for food intake. A significant decrease was seen in abdominal fat with increasing levels of IMO in the feed. (Table 5)

TABLE 5

Accumulation of abdominal fat in rats after 6 weeks at various concentration of isomaltooligosaccharides

| Concentration of Isomaltooligosaccharides (gm IMO/gm food) | Abdominal fat (gm)/ Food Intake (gm) |
| --- | --- |
| 0 | 0.0012 |
| 0.05 | 0.00075 |
| 0.10 | 0.00063 |
| 0.20 | 0.000316 |

These data indicate that IMO-supplemented food is nontoxic. More importantly, this indicates that IMO-supplemented food can reduce either the formation or deposition of fat. It is also predicted that the blood glucose level will be less in rats fed the IMO-supplemented food.

EXAMPLE 9

Effect of Isomaltooligosaccharides-Supplemented Food on Blood Glucose

To determine the effectiveness of IMOs produced as described in Example 2 on blood sugar levels after eating, rats will be used. The rats will be fed IMO-supplemented food as described above in Example 8, and the blood glucose levels monitored overtime after feeding. It is expected that the blood sugar levels in the IMO-fed rats will rise at a slower rate than the controls based on the data above showing that these IMOs are effective α-glucosidase inhibitors (Example 6). It is also predicted that the insulin level will be decreased. This indicates that these IMOs would be effective therapeutically for diabetes or pre-diabetes.

The complete disclosures of all references cited in this application are hereby incorporated by reference. Also, incorporated by reference is the complete disclosure of the following documents: Chang-Ho Chung, "A potential Nutriceutical from *Leuconostoc mesenteroides* B-742 (ATCC 13146); Production and Properties," A dissertation submitted to the Department of Food Science, Louisiana State University, May 2002; and D. F. Day and Chang-Ho Chung, "Probiotics from Sucrose," a slide presentation at the May 22, 2002 meeting of the American Society of Microbiologists. In the event of an otherwise irreconcilable conflict, however, the present specification shall control.

We claim:

1. A method for inhibiting α-glucosidase in a subject in need of delaying the intestinal digestion of starch, starch-derived oligosaccharides, or disaccharides, said method comprising orally administering to the subject an effective amount of a composition comprising one or more maltosyl-isomaltooligosaccharides with only α-1,4 and α-1,6 linkages and with a degree of polymerization less than or equal to 7, wherein the subject has a condition selected from the group consisting of obesity, gastritis, gastric ulcer, duodenal ulcer, hyperglycemia, hyperinsulinemia, and diabetes.

2. A method as in claim 1, wherein said maltosyl-isomaltooligosaccharide composition is produced by fermentation of sucrose in the presence of maltose, in a sucrose:maltose ratio of about 2:1, using the microorganism *Leuconostoc mesenteroides* ATCC 13146.

* * * * *